(12) United States Patent
Blumberg, Jr. et al.

(10) Patent No.: US 11,788,979 B2
(45) Date of Patent: Oct. 17, 2023

(54) SYSTEM AND METHOD FOR CHARACTERIZING BIOREACTOR FLUIDS

(71) Applicant: DEKA Products Limited Partnership, Manchester, NH (US)

(72) Inventors: David Blumberg, Jr., Deerfield, NH (US); Michael C. Tilley, Amherst, NH (US); Derek G. Kane, Manchester, NH (US); David C. Nivens, Hollis, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 17/475,683

(22) Filed: Sep. 15, 2021

(65) Prior Publication Data

US 2022/0003700 A1   Jan. 6, 2022

Related U.S. Application Data

(60) Continuation of application No. 16/881,502, filed on May 22, 2020, now Pat. No. 11,125,706, which is a
(Continued)

(51) Int. Cl.
*G01N 24/08* (2006.01)
*G01R 33/3873* (2006.01)
(Continued)

(52) U.S. Cl.
CPC .......... *G01N 24/088* (2013.01); *C12M 47/04* (2013.01); *G01R 33/307* (2013.01);
(Continued)

(58) Field of Classification Search
CPC .............. G01N 24/088; G01N 24/085; G01R 33/383; G01R 33/3873; G01R 33/445; G01R 33/307; G01R 33/465
See application file for complete search history.

(56) References Cited

U.S. PATENT DOCUMENTS

| 4,617,516 A | 10/1986 | Schenck |
| 5,311,135 A | 5/1994 | Vavrek et al. |

(Continued)

FOREIGN PATENT DOCUMENTS

| DE | 10 2017 205485 | 10/2018 |
| JP | 5112017 | 1/2013 |
| KR | 101958326 | 3/2018 |

OTHER PUBLICATIONS

PCT/US2017/019214, ISR and Written Opinion of the International Search Authority, dated Apr. 9, 2019.
(Continued)

*Primary Examiner* — Dominic E Hawkins
(74) *Attorney, Agent, or Firm* — Mark E. Tetreault

(57) ABSTRACT

A magnetic resonance device for monitoring growth of tissue in one or more bioreactors. The device can include a first magnet and a second magnet that can form a uniform magnetic field of desired strength around at least one sample of effluent from at least one bioreactor. At the command of a controller, an RF signal can illuminate the at least one magnetized sample, and sensors can detect at least one echo signal from the at least one magnetized sample. The controller can characterize the at least one sample based on the at least one echo signal. A resonator can shape the at least one echo signal.

19 Claims, 18 Drawing Sheets

Related U.S. Application Data division of application No. 16/205,820, filed on Nov. 30, 2018, now Pat. No. 10,663,417.

(60) Provisional application No. 62/701,251, filed on Jul. 20, 2018, provisional application No. 62/593,408, filed on Dec. 1, 2017.

(51) Int. Cl.

| | |
|---|---|
| *G01R 33/465* | (2006.01) |
| *G01R 33/30* | (2006.01) |
| *G01R 33/383* | (2006.01) |
| *H01F 7/02* | (2006.01) |
| *C12M 1/00* | (2006.01) |
| *G01R 33/44* | (2006.01) |

(52) U.S. Cl.
CPC ....... *G01R 33/383* (2013.01); *G01R 33/3873* (2013.01); *G01R 33/445* (2013.01); *G01R 33/465* (2013.01); *H01F 7/0226* (2013.01); *G01N 24/085* (2013.01)

(56) References Cited

U.S. PATENT DOCUMENTS

| | | | |
|---|---|---|---|
| 5,382,904 | A | 1/1995 | Pissanetzky |
| 5,935,065 | A | 8/1999 | Rose, Jr. et al. |
| 6,163,154 | A | 12/2000 | Anderson et al. |
| 6,577,125 | B2 | 6/2003 | Prammer et al. |
| 9,433,718 | B2 | 9/2016 | Jones |
| 9,957,439 | B2 | 5/2018 | Van Oort et al. |
| 10,598,745 | B2 | 3/2020 | Niemann et al. |
| 2008/0077074 | A1 | 3/2008 | Keenan et al. |
| 2009/0128272 | A1 | 5/2009 | Hills |
| 2009/0146658 | A1* | 6/2009 | McDowell ........... G01R 33/302 324/309 |
| 2009/0197294 | A1 | 8/2009 | Rapoport |
| 2016/0009007 | A1 | 1/2016 | Araki et al. |
| 2016/0124062 | A1 | 5/2016 | Taicher |
| 2016/0334348 | A1 | 11/2016 | Jones |
| 2017/0285122 | A1 | 10/2017 | Kaditz et al. |
| 2018/0136149 | A1 | 5/2018 | Braumann et al. |
| 2018/0176558 | A1 | 6/2018 | Sugio et al. |

OTHER PUBLICATIONS

Bauer, C. et al., Design of a permanent magnet with a mechanical sweep suitable for variable-temperature continuous-wave and pulsed EPR spectroscopy, Journal of Magnetic Resonance, Academic Press, Orlando, FL, US, 198:2, Jun. 1, 2009, pp. 222-227, FIGs. 1,2, Results and discussion, Magnet design.

Danieli, Ernesto et al., Mobile Nuclear Magnetic Resonance, eMagRes, Jun. 15, 2012, Wiley & Sons, Ltd., ISBN: 978-0-470-03459-0, pp. 849-861, Closed Magnets, FIGs. 5, 8, 9.

Kreyenschulte, Dirk at al., Online monitoring of fermentation processes via non-invasive low-field NMR: online-NMR for Fermentation Processes, Biotechnology and Bioengineering, 112:9, Apr. 7, 2015, pp. 1810-1821, Materials and Methods, Results and Discussion, FIGs. 1-3, 5-7.

Lee, C-S et al., Microwave Resonator for Eye Tracking, IEEE Transactions on Microwave Theory and Techniques, Jun. 12, 2019.

National Research Council. 2003. Beyond the Molecular Frontier: Challenges for Chemistry and Chemical Engineering. Washington, DC: The National Academies Press. https://doi.org/10.17226/10633, Chapter 5, https://www.ncbi.nlm.nih.gov/books/NBK207662/.

Oxford Instruments, MQC Benchtop QA systems from the NMR specialists, http://photos.labwrench.com/equipmentManuals/17920-6352.pdf referenced Oct. 17, 18.

Phuc, Hung Dang et al., Design and Construction of Light Weight Portable NMR Halbach Magnet, International Journal of Smart Sensing and Intelligent Systems, Dec. 1, 2014, 7:4, pp. 1555-1578, http://s2is.org/Issues/v7/n4/papers/paper6.pdf (retrieved on Jul. 25, 2016), IV. Prototype Design and Experimental Set Up, FIGs. 14, 15.

Simmler et al., Universal Quantitative NMR Analysis of Complex Natural Samples, Curr. Opin. Biotechnol., Feb. 2014, pp. 51-59.

Vogel, Michael W et al., Rotatable Small Permanent Magnet Array for Ultra-Low Field Nuclear Magnetic Resonance Instrumentation: A Concept Study, Plos One 11:6, Jun. 6, 2016, pp. 1-24, Materials and Methods, FIGs. 2, 6, SPMA design, Manual SPMA.

U.S. Appl. No. 16/881,502, dated May 22, 2020.

U.S. Appl. No. 16/205,820, dated Nov. 20, 2018.

* cited by examiner

SYSTEM AND METHOD FOR CHARACTERIZING BIOREACTOR FLUIDS

CROSS REFERENCE TO RELATED APPLICATIONS

This application is a Continuation of U.S. patent application Ser. No. 16/881,502, filed May 22, 2020 and entitled SYSTEM AND METHOD FOR CHARACTERIZING BIOREACTOR FLUIDS, which will be U.S. Pat. No. 11,125,706, issuing on Sep. 21, 2021, which is a Continuation of U.S. patent application Ser. No. 16/205,820, filed Nov. 30, 2018 and entitled SYSTEM AND METHOD FOR CHARACTERIZING BIOREACTOR FLUIDS, now U.S. Pat. No. 10,663,417, issued May 26, 2020, which claims the benefit of U.S. Provisional Application Ser. No. 62/593,408, filed Dec. 1, 2017, entitled SYSTEM AND METHOD FOR CHARACTERIZING BIOREACTOR FLUIDS, and U.S. Provisional Application Ser. No. 62/701,251, filed Jul. 20, 2018, entitled SYSTEM AND METHOD FOR CHARACTERIZING BIOREACTOR FLUIDS, which are incorporated herein by reference in their entireties.

BACKGROUND

The present teachings relate generally to tissue engineering, and more specifically to systems and methods to monitor tissue growth.

Magnetic resonance can be used to characterize the composition of materials by taking advantage of the different resonant frequencies of molecular structures. Nuclear magnetic resonance (NMR) involves applying a magnetic field to the material, and the composition of the material determines the frequency of the resonance. When resonance is achieved, the material is illuminated for a short time with a radio frequency (RF) signal at the frequency of the resonance. When the material is illuminated, the material absorbs some of the signal's energy. When there is no illumination, the material will echo some of the absorbed energy back out. The echo can be used to identify the material. By systematically adjusting the magnetic field gradient and signal's pulse waveform, the echo can be converted into an image that enables tissue monitoring. NMR devices can be any size. Smaller NMR devices can include permanent magnets and can be used to measure high-resolution NMR spectra. Advances in real-time magnetic resonance techniques can be used to detect moving fluid as it passes through the magnetic field of the magnetic resonance apparatus. Real-time magnetic resonance techniques include continuous data acquisition and iterative reconstruction, and can be used to create a differenced picture of the temporal variation of the tissue growth based on effluent flowing through a growing tissue enclosure.

Currently, desktop NMR devices weigh between about 42 pounds and 375 pounds. A lighter device, geared for production settings, can be cost-effective to build and use. A device that can analyze multiple samples simultaneously can enable rapid tissue analysis.

SUMMARY

Systems and methods for characterizing tissue samples from, for example, but not limited to, a bioreactor, can include magnet configurations such as magnets that are positioned by rotation, and magnets that are positioned by lateral movement. Magnet positioning, in conjunction with magnetic field spreaders, can provide a stable magnetic field from which reliable measurements can be taken.

The apparatus of the present teachings of a first configuration for identifying contents of effluent from at least one tissue bioreactor can include, but is not limited to including, a rotatable magnet, and at least one container including the effluent. The at least one container can be positioned in proximity to the rotatable magnet. The apparatus can include a second magnet positioned in proximity to the at least one container. The second magnet can be positioned to form a magnetic field across the effluent. The apparatus can include an adjustment means that can rotate the rotatable magnet to adjust the strength of the magnetic field, and a transmitter that can periodically transmit a non-ionizing signal across the magnetized effluent. The non-ionizing signal can energize the magnetized effluent. The apparatus can include a receiver receiving a first at least one echo signal from the magnetized energized effluent based on the non-ionizing signal, and a controller controlling the transmitter, the receiver, and the adjustment means by means of commands. The controller can characterize the first at least one echo signal, and can identify the contents of the effluent based on the characterized first at least one echo signal. The apparatus can optionally include a steel block positioned in proximity to the second magnet. The rotatable magnet can optionally include a cylindrical shape. The apparatus can optionally include a spreader that can be operably positioned between the rotatable magnet and the second magnet. The spreader can enable uniformity of the magnetic field. The rotatable magnet can optionally include a diametric magnetization vector. The diametric magnetization vector can be substantially perpendicular to the spreader. The apparatus can optionally include a resonator that can shape the transmitted non-ionizing signal. The apparatus can optionally include a resonator that can shape the received echo signal. The apparatus can optionally include a positioner that can adjust the strength of the magnetic field based on the position of the second magnet. The positioner can optionally respond to the commands from the controller. The non-ionizing signal can optionally include an RF signal. The apparatus can optionally include an electronic signal generator. The signal generator can supply the non-ionizing signals, and can respond to the commands from the controller. The adjustment means can optionally include a stepper motor. The apparatus can optionally include a temperature sensor that can provide temperature data to the controller. The controller can command the signal generator to adjust, based on the temperature data, the center frequency of the electronic signal to accommodate magnetic drift.

The method of the present teachings for a first configuration for characterizing at least one sample from at least one bioreactor using a magnetic resonance apparatus, where the magnetic resonance apparatus includes a first magnet and a second magnet, and where the first magnet and the second magnet are positioned to set up a magnetic field, the method can include, but is not limited to including, determining a desired magnetic field strength for the magnetic field, rotating the first magnet and positioning the second magnet to achieve the desired magnetic field strength, circulating the at least one sample in the magnetic field, periodically illuminating the at least one sample with an electronic signal, sensing a first at least one echo signal between the illuminations, and characterizing the at least one sample based on the first least one echo signal. The first magnet can optionally include a diametric magnetization vector. The diametric magnetization vector can be substantially perpendicular to a spreader. The spreader can optionally include operable coupling with the second magnet. The electronic signal can travel a first path, and the first path can include at least one tank circuit, at least one coil, and the at least one sample. The method can optionally include directing the at least one electronic signal using the at least one tank circuit. The electronic signal can optionally include an RF signal. The at least one echo signal can optionally travel a second path. The second path can optionally include at least one tank circuit and at least one coil. The method can optionally include rotating the first magnet to achieve a changed magnetic field strength and a changed magnetic field, circulating the at least one sample through the changed magnetic field, periodically illuminating the at least one sample with the electronic signal, sensing a second at least one echo signal between the illuminations, and characterizing the at least one sample based at least on a comparison between the second at least one echo signal and the first least one echo signal. The characterizing can optionally include envelope detection and curve fit.

The system of the present teachings of a second configuration for characterizing at least one sample from at least one bioreactor can include, but is not limited to including, an enclosure forming a path for a magnetic field. The enclosure can include a plurality of cavities that can accommodate a first magnet, a second magnet, a first positioning means, a second position means, a first slug, and a second slug. The first magnet and the second magnet can be positioned a pre-selected distance from one another within two of the cavities. The first slug can positioned between the first magnet and the enclosure. The first slug and the second slug can include including magnetic material, and the second slug can be positioned between the second magnet and the enclosure. The system can include a controller that can control the first positioning means and the second positioning means to position the first slug and the second slug to shape the uniformity of the magnetic field using variable reluctance to create a uniform magnetic field. The controller can enable circulation of the at least one sample in the magnetic field. The sample can be associated with at least one coil. The controller can periodically illuminate the at least one sample and the at least one coil with an RF signal. The controller can sense at least one echo signal between the illuminations, and the controller can characterize the at least one sample based on the sensed least one echo signal. The system can optionally include a position lock means fixing the positions of the first slug and the second slug when the uniform magnetic field is achieved. The system can optionally include a sample tube encircled by the at least one coil. The sample tube can rest between the first magnet and the second magnet, and can provide a channel for the at least one sample. The system can optionally include non-stick material surrounding the first slug and the second slug. The system can optionally include non-stick material surrounding the first slug and the second slug and a resonator shaping the at least one echo signal.

The method of the present teachings of a second configuration for characterizing at least one sample from at least one bioreactor using a magnetic resonance apparatus, where the magnetic resonance apparatus can include a first magnet and a second magnet, and where the first magnet and the second magnet can be positioned a pre-selected distance from one another to set up a magnetic field, and where the first magnet and the second magnet can be positioned within an enclosure forming a path for the magnetic field, the method can include, but is not limited to including, positioning a first slug between the first magnet and the enclosure, and positioning a second slug between the second magnet and the enclosure. The first slug and the second slug can include magnetic material. The method can include shaping the uniformity of the magnetic field using variable reluctance, to create a uniform magnetic field, by adjusting the positions of the first slug and second slug. The method can include circulating the at least one sample in the uniform magnetic field. The sample can be associated with at least one coil. The method can include periodically illuminating the at least one sample and the at least one coil with an electronic signal, sensing at least one echo signal between the illuminations, and characterizing the at least one sample based on the sensed least one echo signal. The method can optionally include fixing the positions of the first slug and the second slug when the uniform magnetic field is achieved. The at least one coil can optionally be about 1 mm in thickness. The at least one sample can optionally be enclosed in a glass tube, the glass tube can optionally be encircled by the at least one coil, and the glass tube can optionally rest between the first magnet and the second magnet. The pre-selected distance between the first magnet and the second magnet can optionally measure about 0.3 inches. The first slug and the second slug can optionally be surrounded by a non-stick material. The method can optionally include manually positioning the first slug and the second slug. The method can optionally include automatically positioning the first slug and the second slug. The method can optionally include automatically circulating the at least one sample, automatically periodically illuminating the at least one sample, automatically sensing the at least one echo signal, and automatically characterizing the at least one sample.

The method of the present teachings for a third configuration for characterizing at least one sample from at least one bioreactor using a magnetic resonance apparatus, where the magnetic resonance apparatus includes a first magnet and a second magnet, and where the first magnet and the second magnet are positioned to set up a magnetic field, the method can include, but is not limited to including, determining a desired magnetic field strength for the magnetic field, rotating the first magnet and positioning the second magnet to achieve the desired magnetic field strength, circulating the at least one sample in the magnetic field, periodically illuminating the at least one sample with an electronic signal, sensing a first at least one echo signal between the illuminations, and characterizing the at least one sample based on the first least one echo signal. The first magnet can optionally include a diametric magnetization vector. The diametric magnetization vector can be substantially perpendicular to a spreader. The spreader can optionally include operable coupling with the second magnet. The electronic signal can travel a first path, and the first path can include at least one antenna, at least one resonator, at least one coil, and the at least one sample. The at least one resonator can be physically isolated from the at least one antenna. The at least one resonator can include, but is not limited to including, at least one tank circuit. The method can optionally include directing the at least one electronic signal using the at least one resonator. The electronic signal can optionally include an RF signal. The at least one echo signal can optionally travel a second path. The second path can optionally include at least one resonator and at least one coil. The method can optionally include rotating the first magnet to achieve a changed magnetic field strength and a changed magnetic field, circulating the at least one sample through the changed magnetic field, periodically illuminating the at least one sample with the electronic signal, sensing a second at least one echo signal between the illuminations, and characterizing the at least one sample based at least on a comparison between the second at least one echo signal and the first least one echo signal. The characterizing can optionally include envelope detection and curve fit.

The method of the present teachings of a fourth configuration for characterizing at least one sample from at least one bioreactor using a magnetic resonance apparatus, where the magnetic resonance apparatus can include a first magnet and a second magnet, and where the first magnet and the second magnet can be positioned a pre-selected distance from one another to set up a magnetic field, and where the first magnet and the second magnet can be positioned within an enclosure forming a path for the magnetic field, the method can include, but is not limited to including, positioning a first slug between the first magnet and the enclosure, and positioning a second slug between the second magnet and the enclosure. The first slug and the second slug can include magnetic material. The method can include shaping the uniformity of the magnetic field using variable reluctance, to create a uniform magnetic field, by adjusting the positions of the first slug and second slug. The method can include circulating the at least one sample in the uniform magnetic field. The sample can be associated with at least one coil. The method can include periodically illuminating the at least one sample and the at least one coil with an electronic signal, sensing at least one echo signal between the illuminations, and characterizing the at least one sample based on the sensed least one echo signal. The method can optionally include directing the electronic signal using a resonator. The at least one coil can optionally include about 1 mm in thickness. The method at least one sample can optionally be enclosed in a glass tube, and the glass tube can optionally be encircled by the at least one coil. The glass tube can optionally rest between the first magnet and the second magnet. The pre-selected distance between the first magnet and the second magnet can optionally include about 0.3 inches. The first slug and the second slug can optionally be surrounded by a non-stick material. The method can optionally include manually positioning the first slug and the second slug. The method can optionally include automatically positioning the first slug and the second slug. The method can optionally include controlling the circulating, illuminating, sensing, and characterizing with an automatic controller.

BRIEF DESCRIPTION OF THE DRAWINGS

The present teachings will be more readily understood by reference to the following description, taken with the accompanying drawings, in which:

FIG. 3C-1 is a circuit diagram of a configuration of the tank circuit of the present teachings;

DETAILED DESCRIPTION

Figure 1:
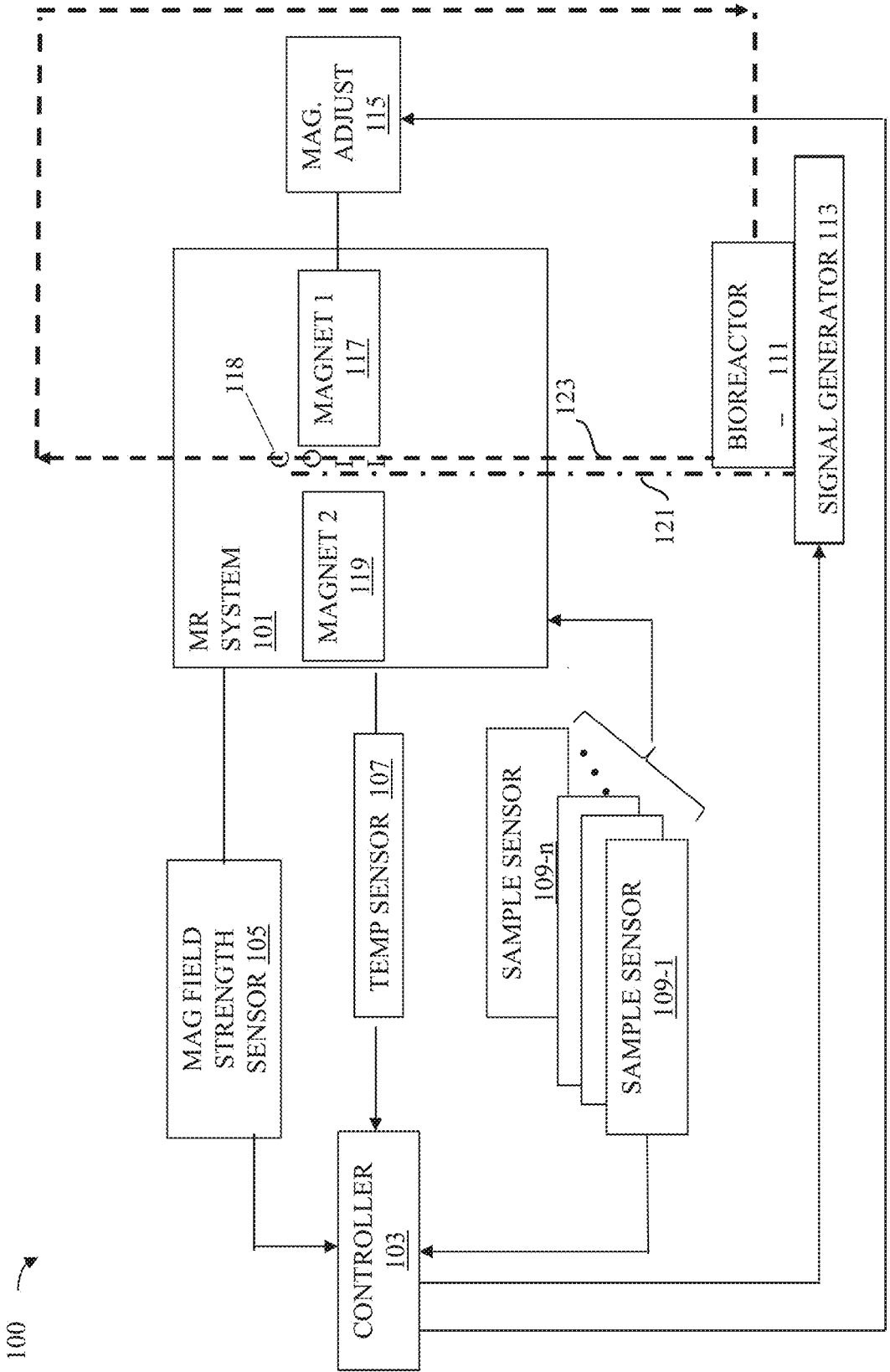
FIG. 1 is a schematic block diagram of the first configuration of the magnetic resonance system of the present teachings.

Referring now to FIG. 1, system 100 can provide a cost-effective way to monitor effluent characteristics continuously. In some configurations, effluent from a tissue growth system can be characterized by exposing at least one sample from, for example, bioreactor 111 to magnetic resonance through, for example, nuclear magnetic resonance (MR) system 101. In some configurations, MR system 101 can include two magnets forming a magnetic field surrounding the effluent. In some configurations, first magnet 117 can be adjusted by magnet adjustment means 115 to form a uniform magnetic field. In some configurations, first magnet 117 can include a rotating magnet, and adjustment means 115 can include, but is not limited to including, a stepper motor. By adjusting first magnet 117, the field strength between first magnet 117 and second magnet 119 can be adjusted, which can likewise adjust the frequency of the resonance of sample 123. In some configurations, the strength of the magnetic field can be ≥0.3 T.

Continuing to refer to FIG. 1, system 100 can include magnetic field strength sensor 105 that can provide information about the magnetic field to controller 103. Controller 103 can adjust first magnet 117 based at least on the data provided by magnetic field strength sensor 105, and the adjustment can alter the strength of the magnetic field. System 100 can include temperature sensor 107 that can provide temperature data of MR system 101 to controller 103. Controller 103 can determine, for example, magnetic drift based on the temperature data, and can adjust the center frequency of RF signal 121 generated by RF generator 113 to accommodate the magnetic drift. Uniformity of the magnetic field can cause the precession of enough electrons so that the combined energy will be able to be seen on a spectrum analyzer. The precession frequency of the electrons can indicate the characteristics of the sample according to Larmor's equation: $f_0 = \gamma B_0$, where $f_0$ is the precession frequency of the electrons in the sample, $B_0$ is the strength of the magnetic field surrounding the sample, and $\gamma$ is the gyromagnetic ratio, a constant specific to each nucleus or particle. The value of $\gamma$ for an exemplary particle such as, for example, but not limited to $^1H$, is 42.58. Negative values for $\gamma$ indicate that the direction of precession for the nucleus or particle is opposite the direction of precession of $^1$H. The resonance frequency of any particle at a certain field strength can be calculated using the Larmor equation. For example, for $^1$H, when $B_0$=1.5 T, $f_0$=42.58 Mhz/T*1.5 T=63.87 Mhz.

Figure 1A:
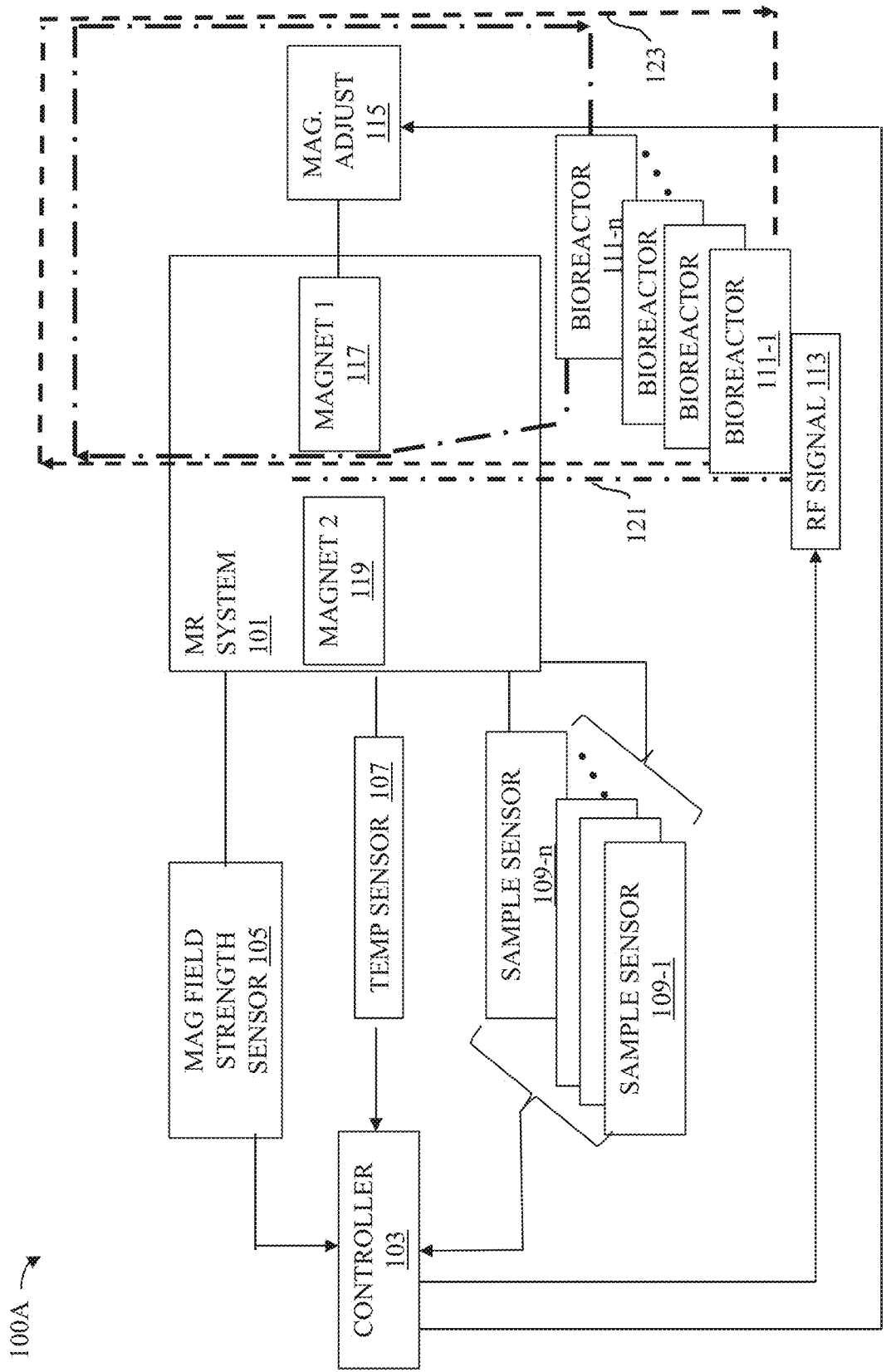
FIG. 1A is a schematic block diagram of a second configuration of the magnetic resonance system of the present teachings.

Referring now to FIG. 1A, in some configurations, system 100A can include sample sensors 109-1 through 109-$n$ that can receive information about constituents of effluent stream 123 that can, for example, cycle through bioreactor 111-1. Sample sensors 109-1 through 109-$n$ can provide sample information to controller 103, and controller 103 can determine characteristics of the constituents. In some configurations, one sample sensor 109-1 can receive and process information about the entire effluent stream. In some configurations, multiple bioreactor streams 123 can emerge from multiple bioreactors 111-1 through 111-$n$ and can be simultaneously analyzed. Multiple bioreactor streams 123 can be illuminated by a single RF coil, and can each be associated with an RF receiver. A resonator can be shaped to direct the signal from the sample to the proper receiver so that controller 103 can associate a sample with a signal.

Figure 1B:
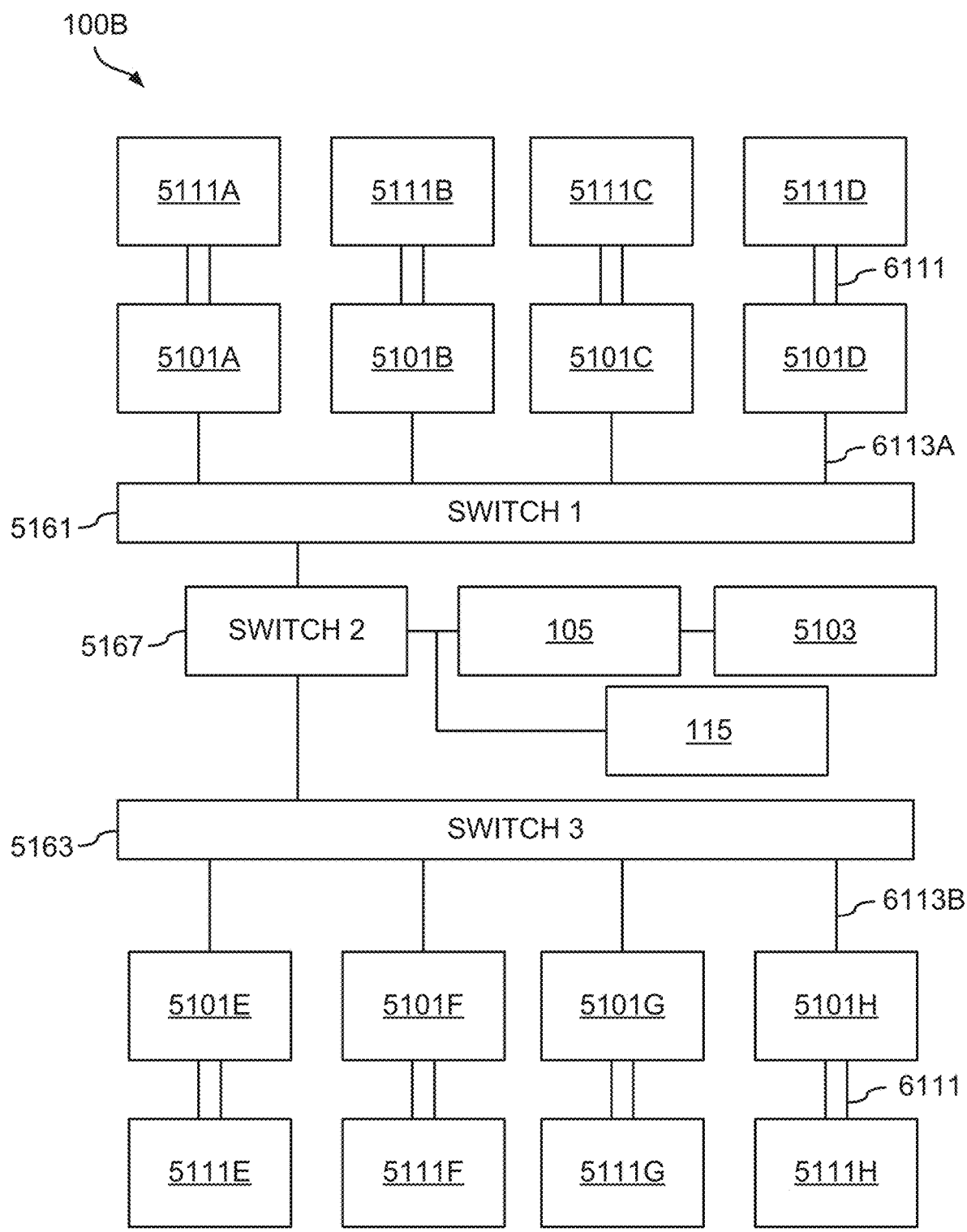
FIG. 1B is a schematic block diagram of the matrix of coils of the present teachings.

Referring now to FIG. 1B, system 100B can include a matrix of coils that can be formed to receive and process information from multiple bioreactor streams simultaneously. The bioreactor streams can originate from a single bioreactor or from multiple bioreactors 5111A-5111H, for example. Multiple streams 6111 can flow through a single MR system 5101A or multiple MR systems 5101A-5101H, for example. Any number of MR systems and bioreactors can be ganged together with any number of switches, not limited to including three switches and eight MR systems, which numbers and configurations set out herein are exemplary only. MR control/data signals 6113A from MR systems 5101A-5101D can be routed through first switch 5161 and second switch 5167, and MR control/data signals 6113B from MR systems 5101E-5101H can be routed through third switch 5163 and second switch 5167. First switch 5161 and third switch 5163 can include four poles each, and can be operably coupled with second switch 5167, which can include two poles, providing for each of eight MR/bioreactor pairs to be separately controlled, depending upon the orientation of the poles in first switch 5161, second switch 5167, and third switch 5163. Other configurations can include, but are not limited including, multiple bioreactor streams flowing into a single MR system, where the single MR system can multiplex signals from the multiple bioreactor streams.

Figure 2:
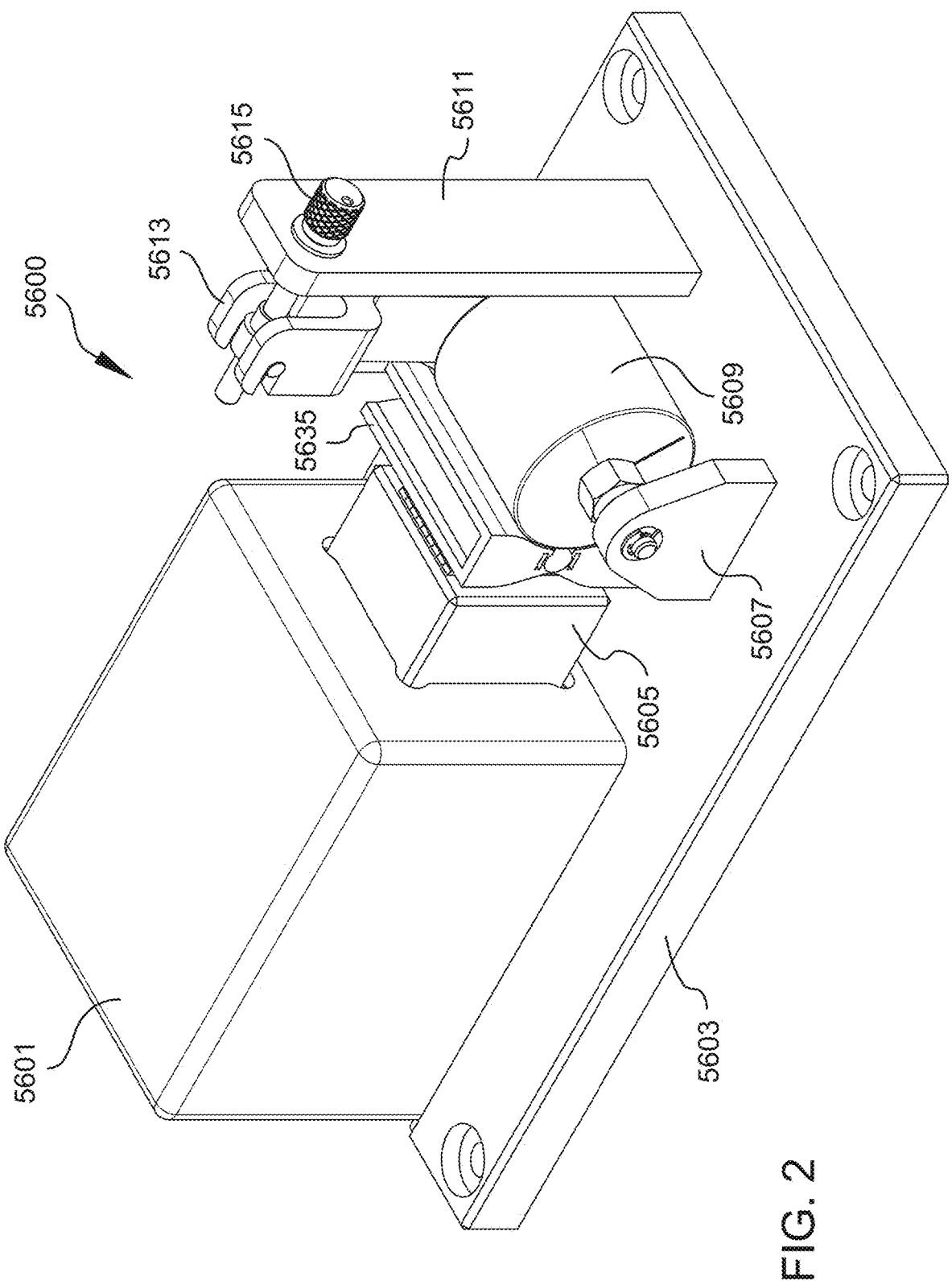
FIG. 2 is a perspective diagram of the first configuration of the magnetic resonance system of the present teachings.
Figure 2A:
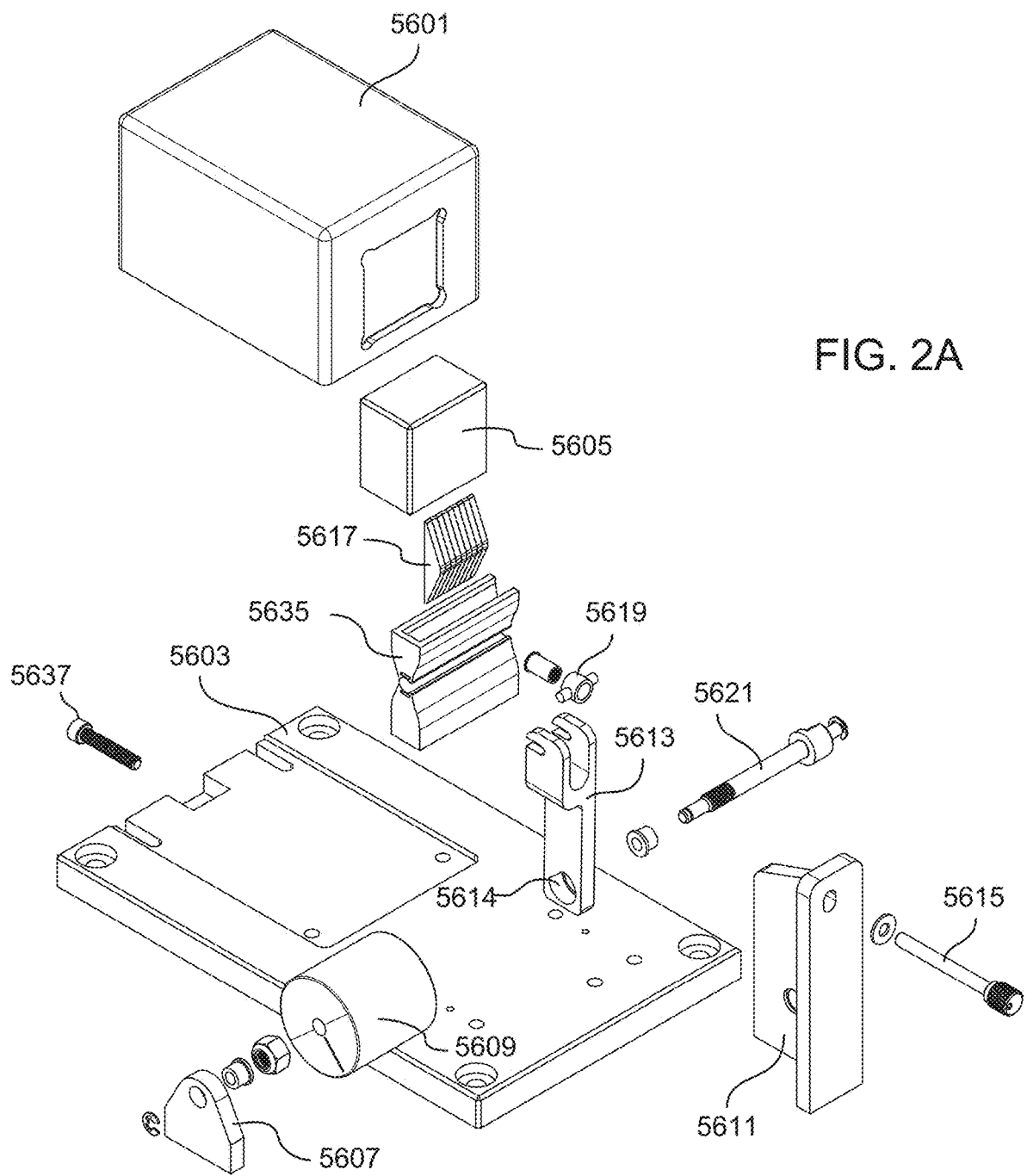
FIG. 2A is an exploded perspective diagram of the first configuration of the magnetic resonance system of the present teachings.
Figure 3:
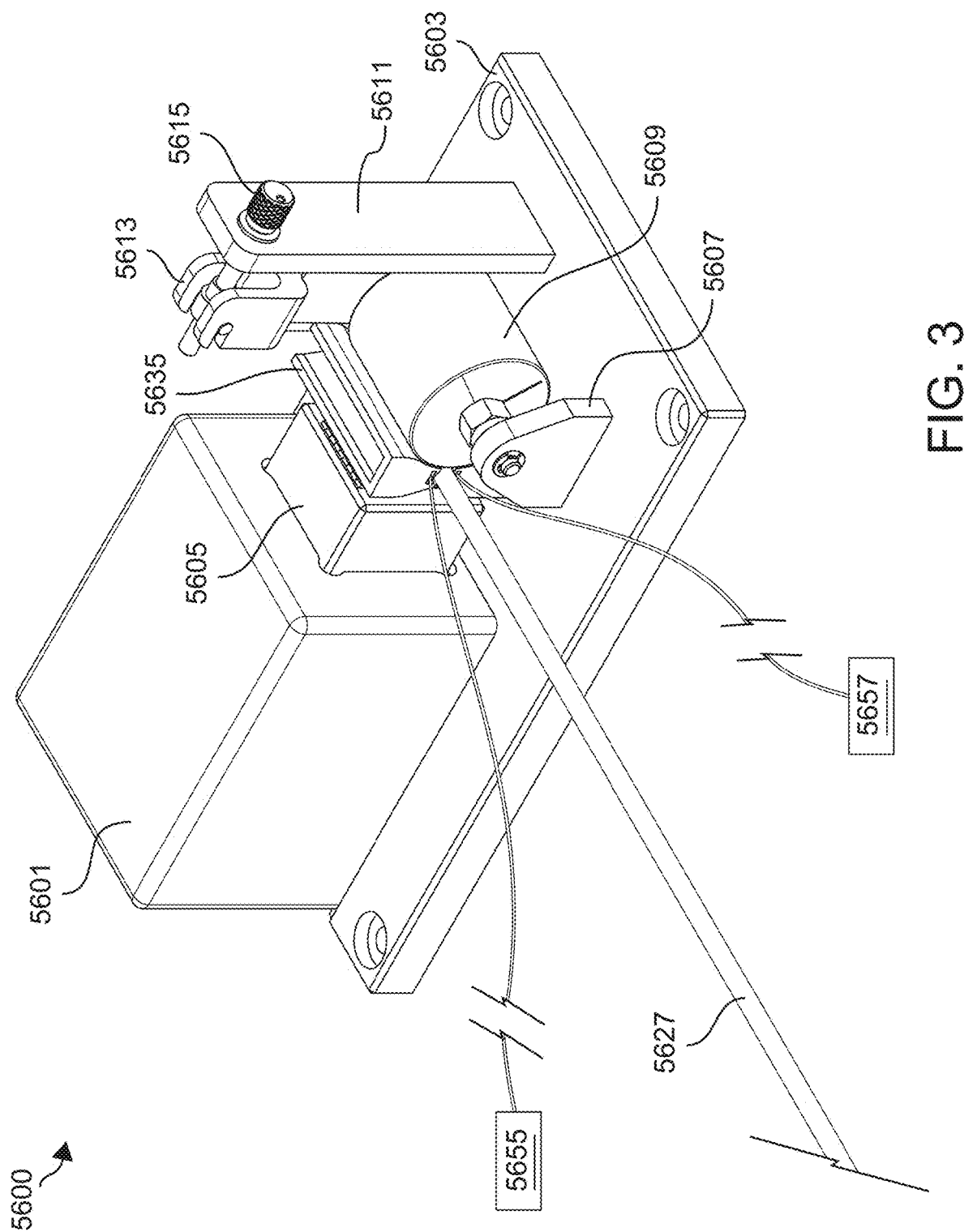
FIG. 3 is a perspective diagram of the first configurations of the magnetic resonance system of the present teachings including a radio frequency apparatus and a bioreactor tube.
Figure 3A:
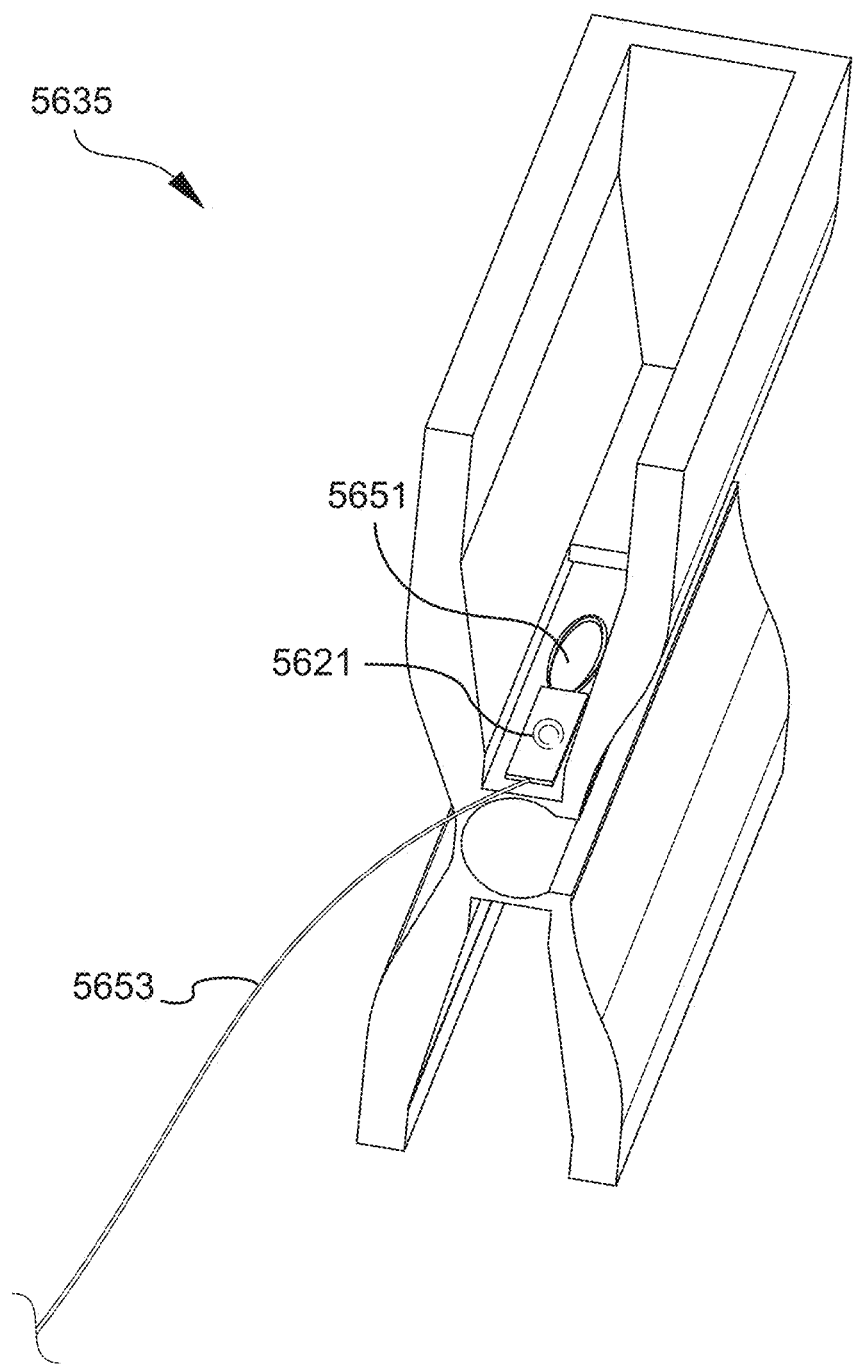
FIG. 3A is a perspective diagram of the coil of the present teachings.

Referring now primarily to FIGS. 2 and 2A, MR apparatus 5600, a configuration of MR system 100 (FIG. 1), can include rectangular magnet 5605, a configuration of magnet 2 119 (FIG. 1) and cylindrical magnet 5609, a configuration of magnet 1 117 (FIG. 1). Rectangular magnet 5605 and cylindrical magnet 5609 can be mounted upon platform 5603, and can be chosen to optimize magnetic field strength to enable the use of relatively small magnets to obtain a relatively large amount of information from the effluent that travels through specimen mount 5635. In some configurations, cylindrical magnet 5609 can measure 1.5" in diameter and one inch in height, but magnet 5609 is not limited to these measurements. With respect to creating a desired magnetic field, magnet 5605 can be moved towards magnet 5609 by installation screw 5637 (FIG. 2A) that can enable controlled placement of magnet 5605 regardless of magnet strength. In some configurations, installation screw 5637 (FIG. 2A) can be operably coupled with controller 103 (FIG. 1), and can move magnet 5605 in accordance with data obtained from magnetic field strength sensor 105 (FIG. 1). A magnet rotation system can enable rotation of cylindrical magnet 5609 to adjust the magnetic field. In some configurations, the magnet rotation system can be operably coupled with controller 103 (FIG. 1), and can rotate magnet 5609 in accordance with data obtained from magnetic field strength sensor 105 (FIG. 1). The magnet rotation system can include, but is not limited to including, strength adjustment means mount 5611 that can securely mount pole adjuster 5615, and link lever arm 5613 upon which pole adjuster 5615 can rest as it is rotated. Pole adjuster 5615 can operably couple with swivel yoke 5619 (FIG. 2A) that can disable rotational adjustment of magnet 5609 at pre-selected settings. Cylindrical magnet mount 5607 can operably couple with alignment pin 5621 (FIG. 2A) and mount guide cavity 5614 (FIG. 2A) that can together enable proper vertical placement of cylindrical magnet 5609. At least one effluent tube 5627 (FIG. 3) can be securely positioned within specimen mount 5635. In some configurations, multiple bioreactors 111-1 through 111-$n$ can produce separate streams of effluent and can require multiple effluent tubes 5627 (FIG. 3). Specimen mount 5635 can include multiple effluent tubes 5627 (FIG. 3), and can accommodate the geometry of magnet 5609 and at least one spreader 5617. At least one spreader 5617 can enable uniformity in the magnetic field, based on the geometry of the magnets and specimen mount 5635.

Continuing to refer to FIGS. 2 and 2A, in some configurations, pole adjuster 5615 can be a screw, and can, in conjunction with link lever arm 5613, perform high resolution rotation of magnet 5609. In some configurations, a desired angular resolution can be chosen, for example, but not limited to, ±0.025°. A combination of thread pitch and distance of lever arm 5613 can be chosen so that magnet 5609 can be rotated in increments smaller than the desired angular resolution if a reasonable minimum articulation angle is chosen, for example, 1/16 of a revolution. In some configurations, when the minimum adjustment is chosen to be 16°, the minimum sweep adjustment, as a fraction of a revolution, is 16°/360°. In some configurations, pole adjuster 5615 is a screw having a 3/16-inch thread diameter and 100 threads/inch. Dividing the minimum sweep adjustment by the threads/inch yields displacement/minimum adjustment, or 0.0004 inches/thread. The angular rotation can be calculated as:

$$\arcsin((\text{displacement/minimum adjustment})/\text{length of lever arm 5613})$$

In some configurations, the length of lever arm 5613 can be approximately 2.435 inches, and the angular rotation can equal 0.01050094°. In some configurations, system 5600 can include parts that can, collectively, weigh approximately ten pounds, and can be manufactured economically, for example, for under 500 USD. In some configurations, system 5600 can optionally include a connecter between spreader 5617 (FIG. 3B) and sink 5601 (FIG. 3) that can retain the position of spreader 5617 (FIG. 3B).

Referring now to FIGS. 3, and 3A-3D, energy from a known magnetic field can be applied to an effluent, and a transmitting coil can pulse the non-ionizing RF signal across the effluent. The pulsed non-ionizing RF signal can excite the nuclear spin energy transition of the effluent. The gradient of the magnetic field can be uniform within the measured bandwidth. The magnetic field can surround the effluent that can circulate through a bioreactor (not shown) in effluent tube 5627 (FIG. 3). The bioreactor can include growing tissue, for example. RF transmitter 5657 (FIG. 3) can supply an RF signal to a transmitter coil, for example, coil 5651 (FIG. 3A), cabled to power by cable 5653 (FIG.

Figure 3B:
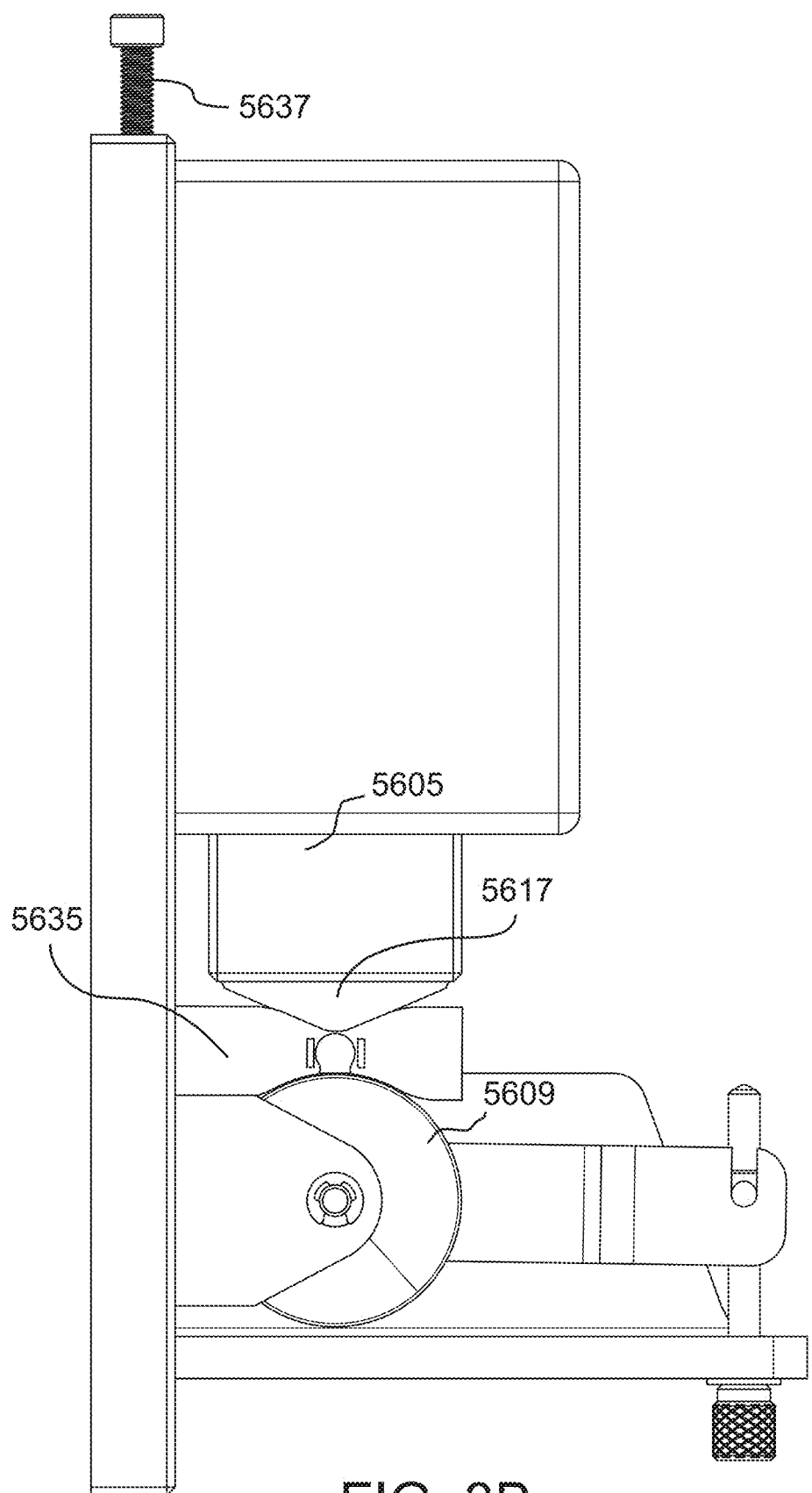
FIG. 3B is a side view of the first configuration of the magnetic resonance system of the present teachings.
Figure 3C:
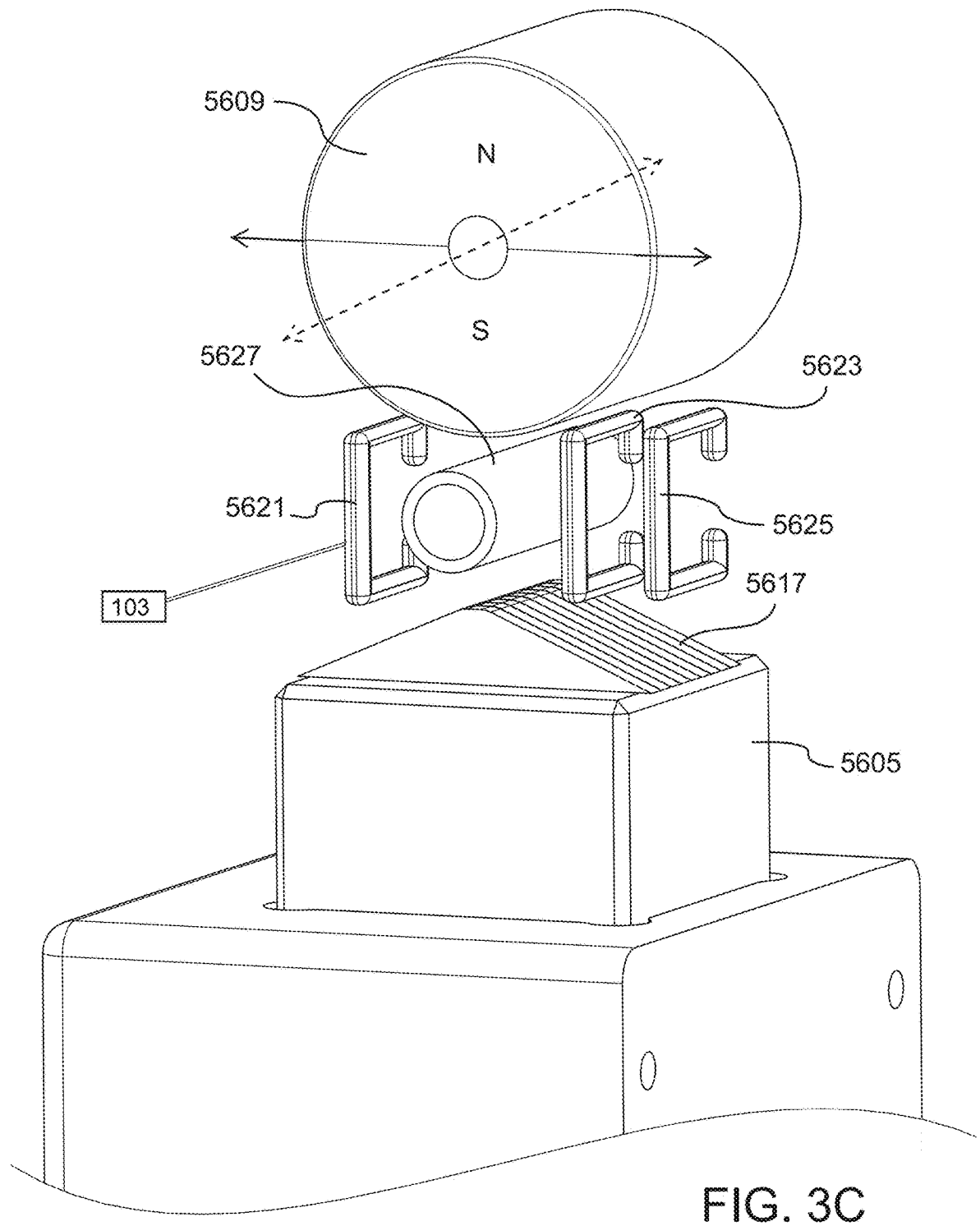
FIG. 3C is an overhead perspective view of the first configuration of the magnetic resonance system of the present teachings.
Figures 1, 3C:
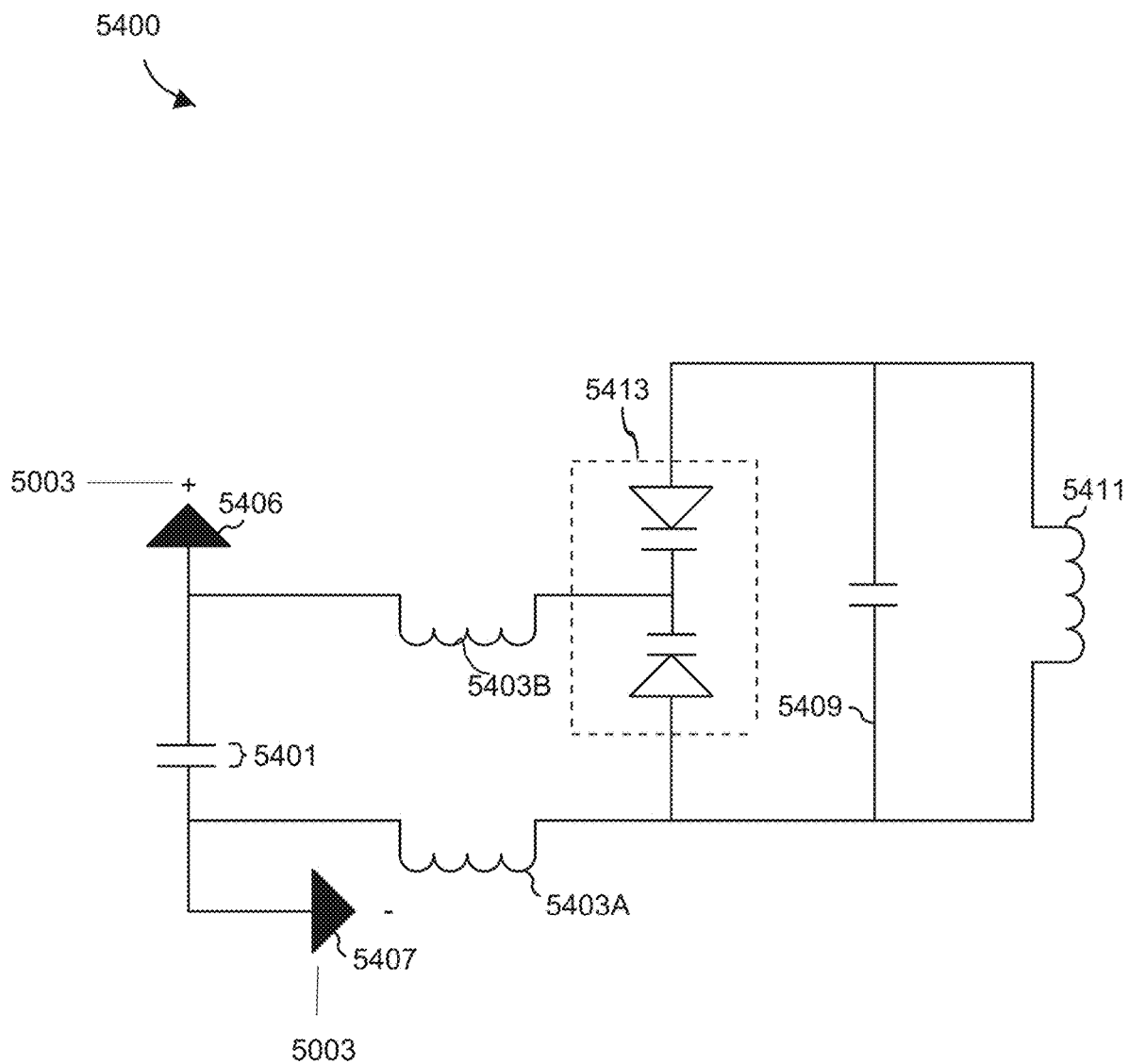
Figure 3D:
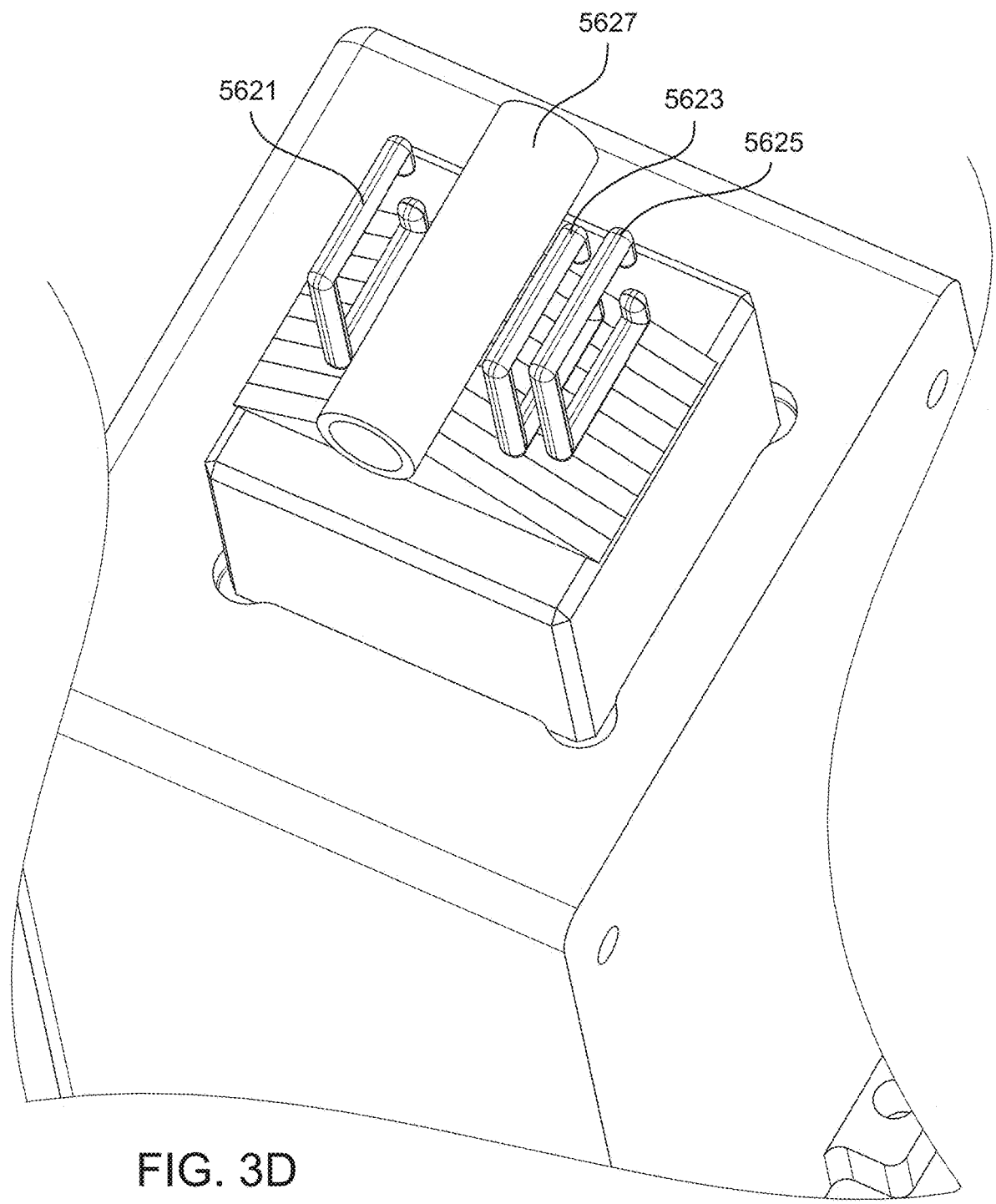
FIG. 3D is a perspective diagram of the effluent passage of the first configuration of the magnetic resonance system of the present teachings.

3A), through at least one transmitter tank circuit 5621/5623/5625 (FIG. 3C), depicted schematically in FIG. 3C-1. At least one transmitter tank circuit 5621/5623/5625 (FIG. 3C) can be adjusted electronically using voltage controlled varactor tuning, for example, to enable drift correction. The choice of the frequency of the RF signal is based upon the atomic structure of the sample and the magnetic field. The magnetic field orients the atoms in the sample, and the pulsing RF signal across the sample makes the atoms resonate at a characteristic frequency that depends on the magnetic field strength. In some configurations, a shielded cable from the source of the RF signal and/or from the sensor to the coil can be included, with the tank circuit oriented in between the sample and the coil. When the RF signal ceases pulsing, the receiving coil can detect the echo from the sample. In some configurations, a single coil can be used to both transmit and receive the RF signal, and can be adjusted electronically as shown in FIG. 3C-1.

Referring now to FIG. 3B, the space between magnets 5605 and 5609 affects the magnetic field strength. In some configurations, magnet 5609 can include a diametric magnet whose diametric magnetization vector can extend from the center of magnet 5609 to the ridge of spreader 5617. In some configurations, magnets 5605/5609 can be chosen such that the magnetic field set up by magnets 5605/5609 can measure approximately 1.2 Tesla, and can have approximately a 501$b$ pull force. Spreader 5617 can be chosen such that the magnetic field, when including spreader 5617, can measure approximately 0.9 Tesla. In some configurations, spreader 5617 can adjust the uniformity of the magnetic field across the sample, and the amount of the adjustment can depend on the geometry of spreader 5617. Spreader 5617 can include a single unit, or can include multiple units, possibly operably coupled. In some configurations, the shape of spreader 5617 can accommodate the geometry of specimen mount 5635.

Referring now to FIG. 3C, at least one transmitter tank circuit 5621/5623/5625 (FIG. 3C) can be constructed to tune the RF signal to a particular frequency. As the effluent circulates near a transmitting coil, for example, but not limited to, coil 5651 (FIG. 3A), which emits non-ionizing electromagnetic energy received from RF transmitter 5657 (FIG. 3), and tuned by at least one transmitter tank circuit 5621/5623/5625, the effluent in effluent tube 5627 (FIG. 3) can respond to the RF signal. The sample's response to the signal can be received by a receiving coil connected to RF receiver 5655 (FIG. 3) via the shielded cable, and tuned by at least one tank circuit 5621/5623/5625. The received tuned signal can be processed by a controller (not shown) to gather data about the effluent. The contents of the effluent can be determined, for example, based on Larmor's equation. There can be any number of tank circuits between RF receiver 5655 (FIG. 3) and the receiving coil, and between RF transmitter 5657 (FIG. 3) and the transmitting coil. The tank circuits can include geometries that are selected to shape the signal strength of the magnetic field. Tank circuits can be used to, for example, but not limited to, focus and direct the RF signal.

Referring now to FIG. 3C-1, circuit 5400 can include coil 5411 and capacitor 5409, along with varactor 5413, that can form an LC-resonant tank circuit. Coil 5411 forms the inductive portion, and capacitor 5409 combined with varactor 5413 form the capacitive portion. Varactor 5413, when reverse biased with a DC voltage 5003, entering circuit 5400 through positive and negative terminals 5406/5407, will behave as a capacitor, with the amount of capacitance controlled by the DC voltage potential. In this arrangement, the resonant frequency of the LC tank circuit can be changed by adjusting the DC voltage on the varactor. In close proximity (approximately 0.1-0.5 inches) to the LC resonant circuit, inductors 5403A and 5403B provide a high impedance at the LC tank resonant frequency, while maintaining a low DC resistance to the varactor control voltage. Similarly, capacitor 5401 provides a high impedance for the varactor control voltage, and a low impedance at the LC tank resonant frequency. In this arrangement, inductors 5403A and 5403B, along with capacitor 5401 can decouple the LC circuit from the DC control voltage circuit. An alternating current electromagnetic energy signal propagating through a non-conductive medium such as, for example, but not limited to, air, foam, or ceramic, in close proximity (approximately 0.1-0.5 inches) to coil 5411 will induce a voltage in coil 5411, creating a storage charge. The charge will continue to grow in potential, additionally charging the capacitive portion formed by capacitor 5409 combined with varactor 5413, until the AC signal reverses polarity. When the AC signal reverses polarity, the stored charge in the inductive portion will flow into the capacitive portion, and vice-versa. The resonant frequency of the LC tank circuit is now controlled by an external DC voltage. Current flowing through coil 5411 back and forth to the capacitive portion of the LC tank circuit will create a secondary magnetic field. This field, by virtue of the geometry of coil 5411 and proximity to transmit and receive coils, for example, coil 5651 (FIG. 3A) of MR system 5635 (FIG. 3A), can be used to shape the transmit signal into the sample, and the received echo signal from the sample.

Figure 4:
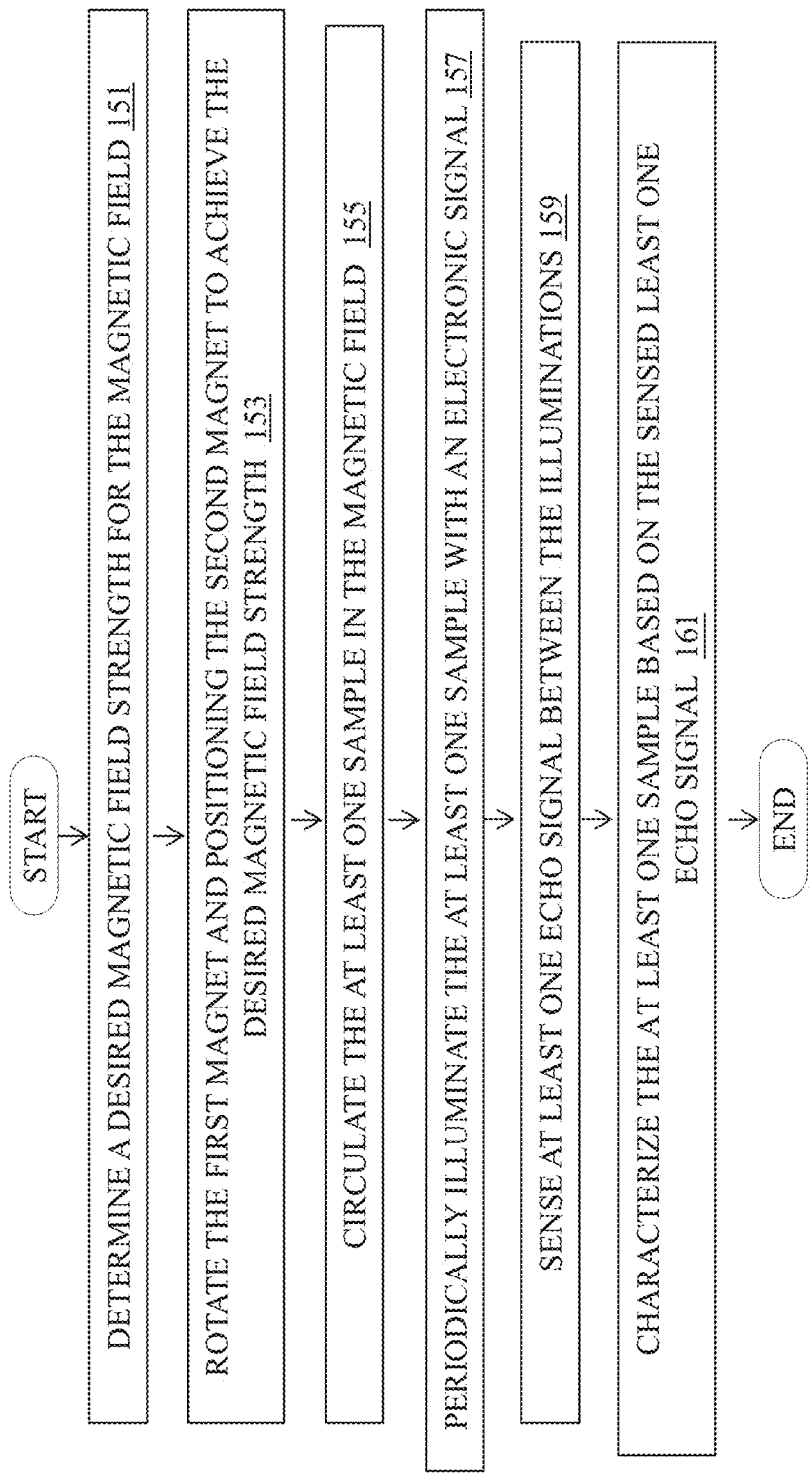
FIG. 4 is a flowchart of the method for characterizing effluent of the present teachings.

Referring now to FIG. 4, method 150 for characterizing at least one sample from at least one bioreactor using a magnetic resonance apparatus, the magnetic resonance apparatus having a first magnet and a second magnet, the first magnet and the second magnet positioned to set up a magnetic field, the method can include, but is not limited to including, determining 151 a desired magnetic field strength for the magnetic field, rotating 153 the first magnet and positioning the second magnet to achieve the desired magnetic field strength, circulating 155 the at least one sample in the magnetic field, periodically illuminating 157 the at least one sample with an electronic signal, sensing 159 at least one echo signal between the illuminations, and characterizing 161 the at least one sample based on the sensed least one echo signal.

Figure 5:
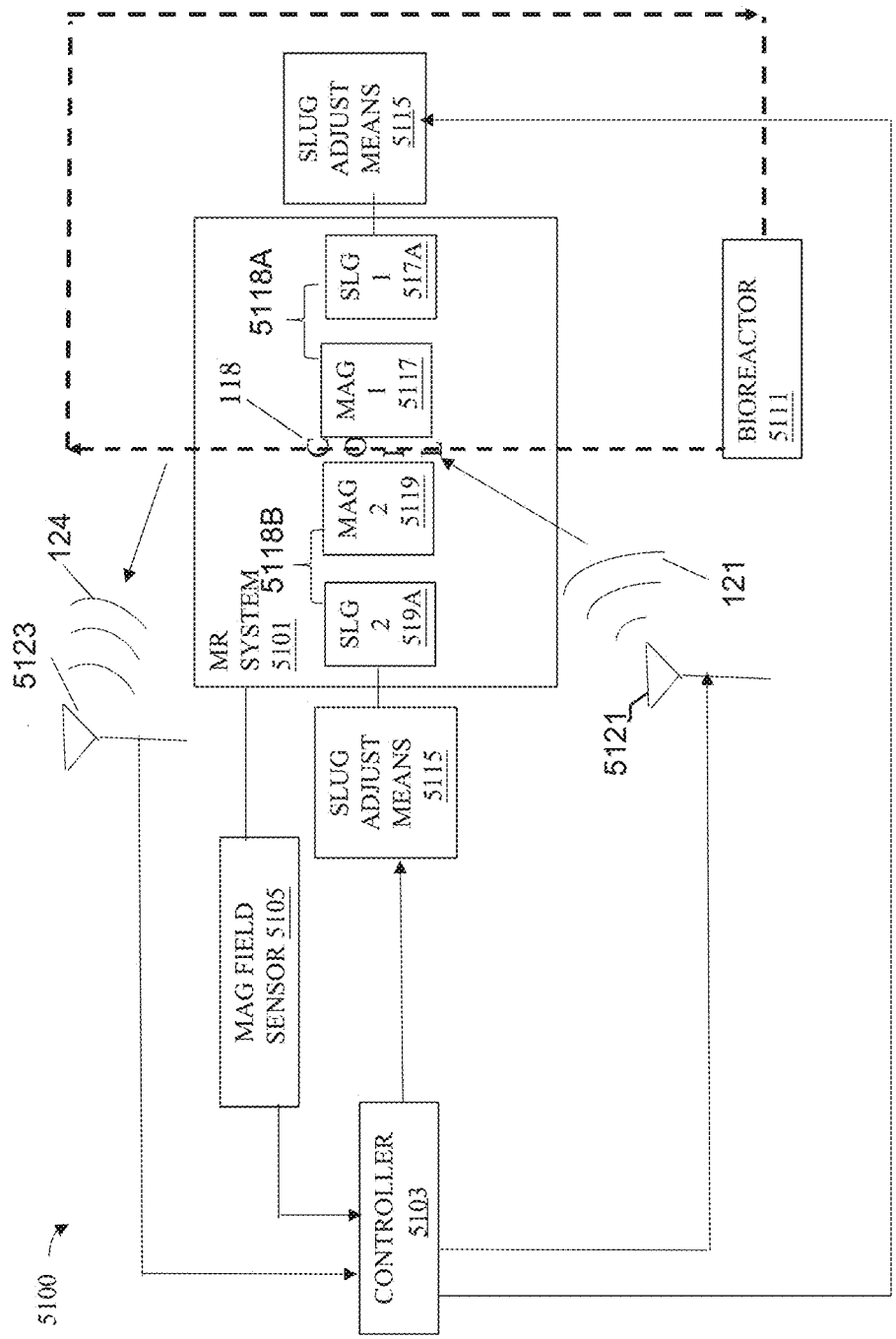
FIG. 5 is a schematic block diagram of the first configuration of the magnetic resonance system of the present teachings.
Figure 6A:
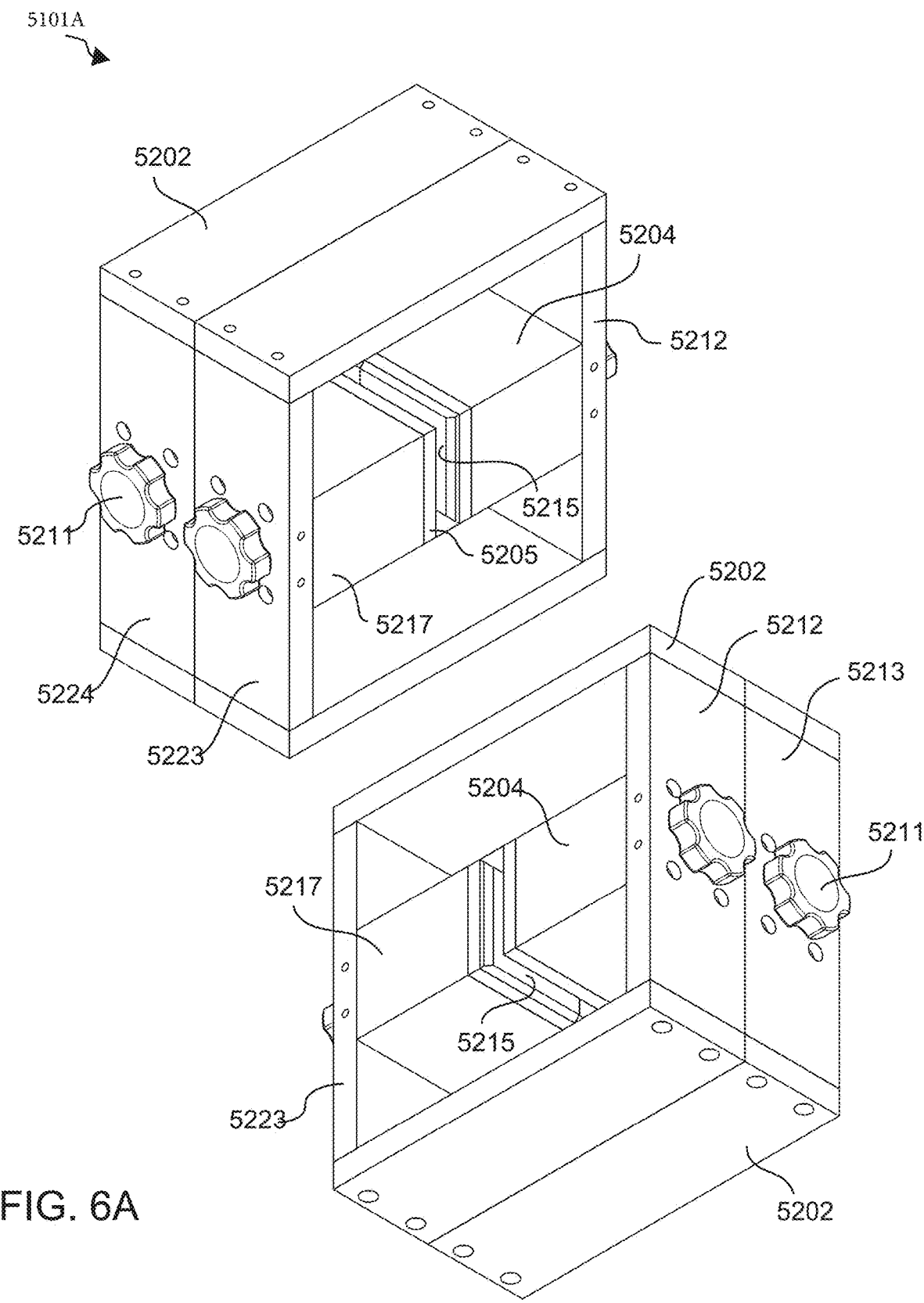
FIGS. 6A-6D are perspective and exploded diagrams of the second configuration of the magnetic resonance system of the present teachings.
Figure 6B:
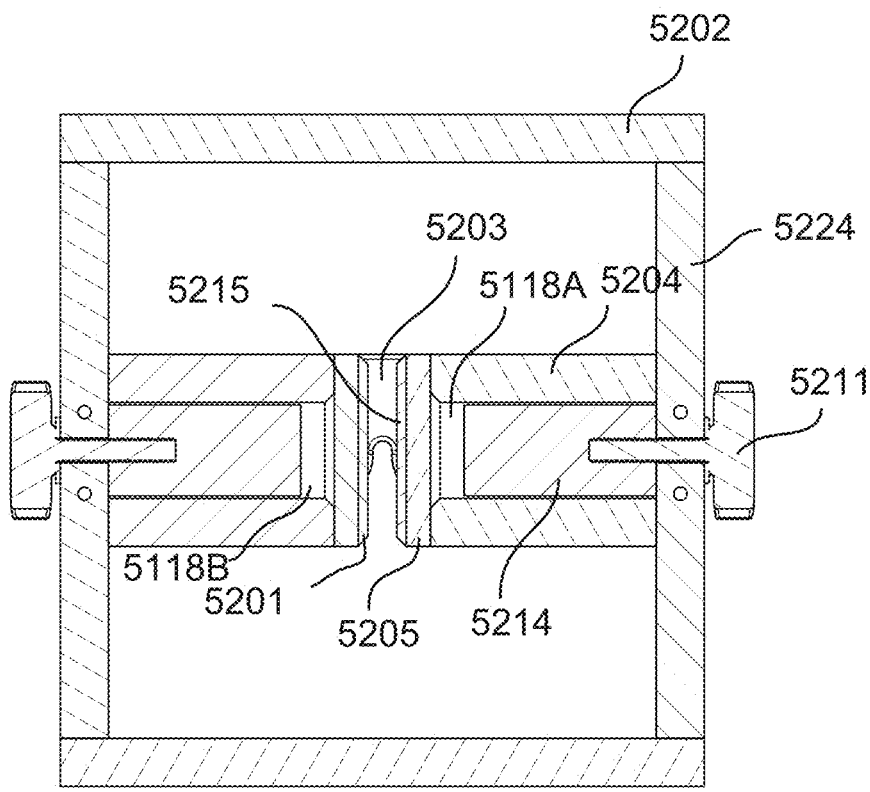
Figure 6C:
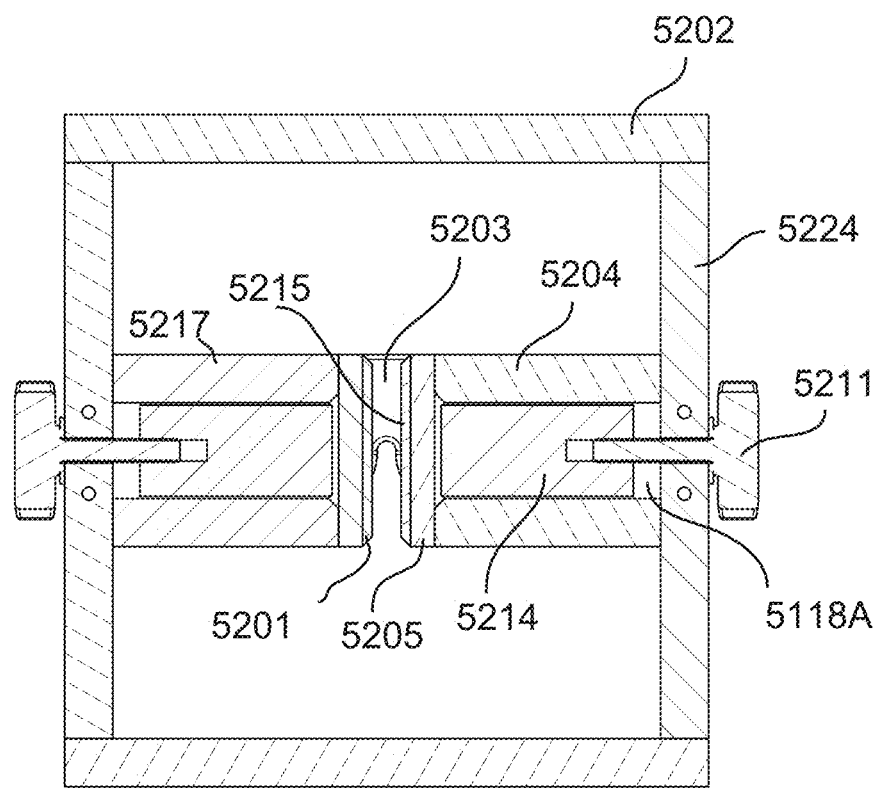

Referring now to FIG. 5, system 5100 can provide a cost-effective way to monitor effluent characteristics continuously. In some configurations, effluent from a tissue growth system can be characterized by exposing at least one sample from, for example, bioreactor 5111 to magnetic resonance through, for example, nuclear magnetic resonance (MR) system 5101. The sample can be conveyed through the magnetic field by a sample carrier (not shown) that can be associated with coil 118. Coil 118 can include a resonator such as, for example, but not limited to, a tank circuit. In some configurations, MR system 5101 can include two magnets forming a magnetic field surrounding the effluent. In some configurations, first magnet 5117 and second magnet 5119 can each include a first side and a second side. The first side of each of first magnet 5117 and second magnet 5119 can be mounted adjacent to enclosures such as, for example, but not limited to, first enclosure 5217 (FIG. 6A) and second enclosure 5204 (FIG. 6A). The second side of each of first magnet 5117 and second magnet 5119 can be at least partially covered by field spreaders such as, for example, but not limited to, first spreader 5215 (FIG. 6C) and second spreader 5201 (FIG. 6C). In some configurations, the distance between first spreader 5215 (FIG. 6C) and second spreader 5201 (FIG. 6C) can be approximately 0.1-0.8 inches. The magnetic field spreaders can, in conjunction with first reluctance path obstruction 5118A and second reluctance path obstruction 5118B, create a uniform magnetic field as first reluctance path obstruction 5118A and second reluctance path obstruction 5118B positions are adjusted. First reluctance path obstruction 5118A and second reluctance path obstruction 5118B can be adjusted by moving first slug 517A and second slug 519A towards or away from first magnet 5117 and second magnet 5119, respectively. Slug adjustment means 5115 can be used to move first slug 517A and second slug 519A. In some configurations, slug adjustment means 5115 can be manual. Slug adjustment means 5115 can include, but is not limited to including, knob 5211 (FIG. 6A). In some configurations, slug adjustment means can be controlled by controller 5103, either locally and/or remotely.

Continuing to refer to FIG. 5, system 5100 can include magnetic field sensor 5105 that can provide information about the magnetic field to controller 5103. Controller 5103 can adjust the position of first slug 517A and second slug 519A based at least in part on data from magnetic field sensor 5105. Controller 5103 can adjust the center frequency of RF signal 121 and can receive and process RF echo signals 124 from the sample. The information about the magnetic field can include, but is not limited to including, strength and uniformity. In some configurations, the strength of the magnetic field can be a function of the position of the resonator, the size of the sample carrier, and the proximity of the magnetic field to the sample carrier. In some configurations, the resonator is optional.

Continuing to refer to FIG. 5, in some configurations, echo signal 124 can provide sample information to controller 5103, and controller 5103 can determine characteristics of the constituents. In some configurations, echo signal 124 can include information from multiple of bioreactors 5111, and controller 5103 can be simultaneously analyze their data. Multiple of bioreactors 5111 can each be associated with, for example a separate RF receiver. At least one transmitter tank circuit (not shown) can be constructed to tune the RF signal to a particular frequency. As the effluent circulates near a transmitting coil, emitting non-ionizing electromagnetic energy received from RF transmitter 5121, and tuned by at least one transmitter tank circuit (not shown), the effluent in the effluent tube (not shown) can respond to RF signal 121. The sample's echo 124 resulting from RF signal 121 can be received by a receiver coil and RF echo receiver 5123, and tuned by at least one tank circuit (not shown). The received tuned signal can be processed by controller 5103 to gather data about the effluent. The contents of the effluent can be determined, for example, based on Larmor's equation. There can be any number of tank circuits between the RF receiver and the receiving coil, and between the RF transmitter and the transmitting coil. The tank circuits can include geometries that are selected to shape the signal strength of the magnetic field. Transmitter 5121 and echo receiver 5123 can be combined so that the RF signal 121 and echo 124 originate and terminate at the same transceiver.

Figure 6D:
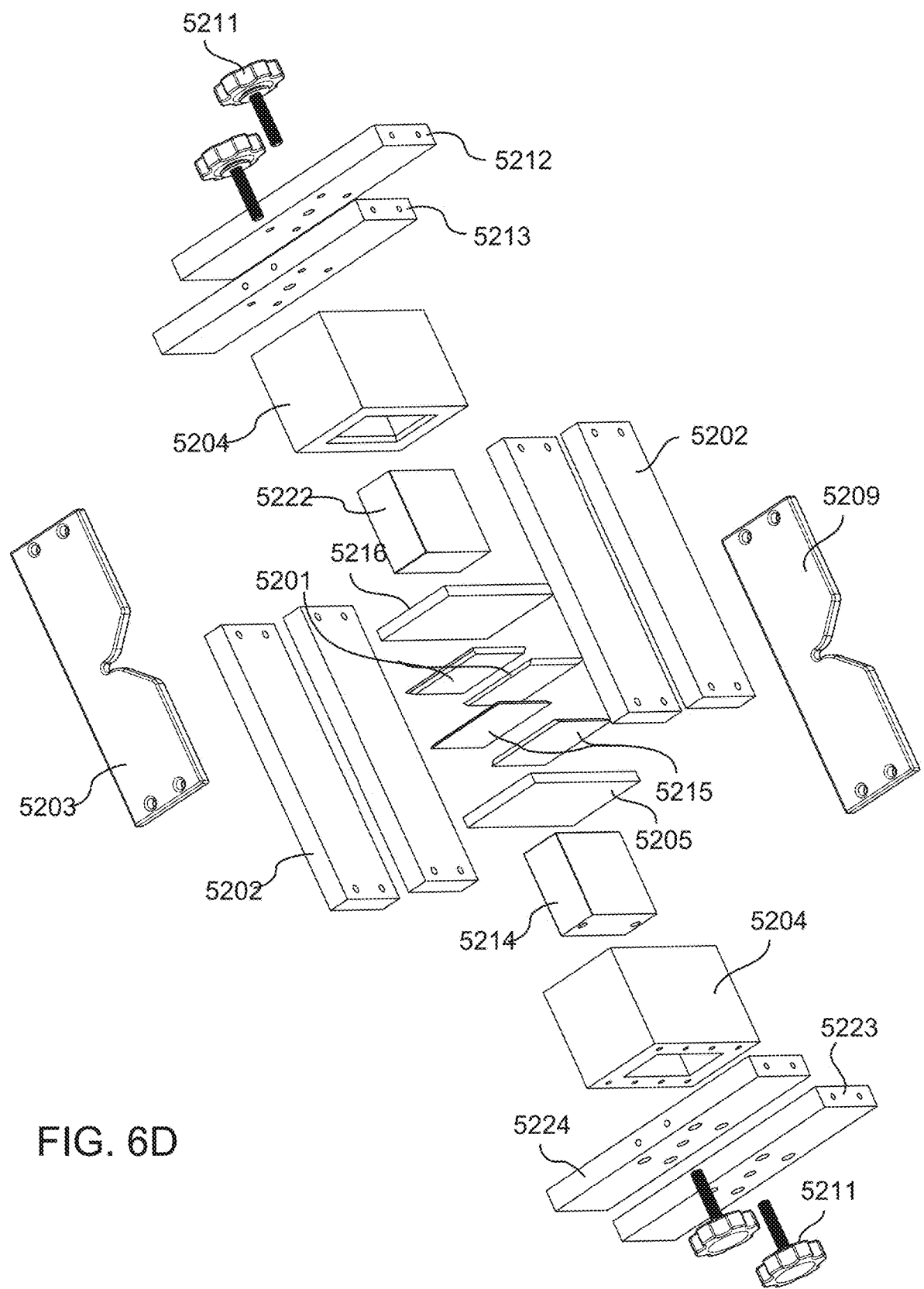
Figure 7:
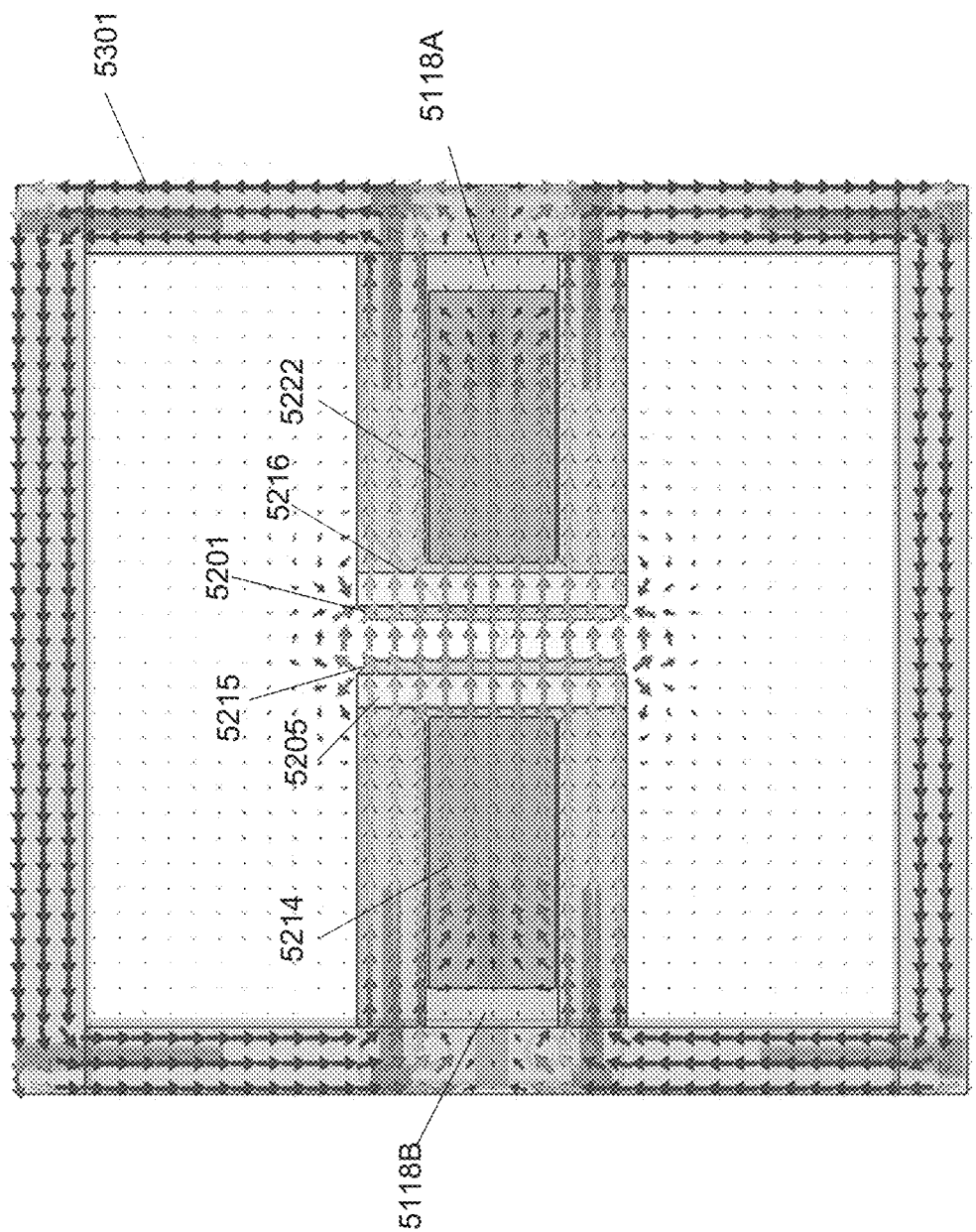
FIG. 7 is a pictorial representation of the magnetic field produced by the magnetic resonance system of the present teachings.

Referring now primarily to FIGS. 6A-6D, system 5101A, a configuration of system 5100 (FIG. 5), can include magnet 5216, a configuration of first magnet 5117 (FIG. 5), and magnet 5205, a configuration of second magnet 5119 (FIG. 5). Magnet 5216 and magnet 5205 can be chosen to optimize magnetic field strength and uniformity to enable the use of relatively small magnets to obtain a relatively large amount of information from the effluent that travels through a specimen tube (not shown) resting in specimen mount 5203/5209. In some configurations, magnets 5205/5216 can be rectangular in shape, and can measure about 4"×2"× 0.25". Other magnet sizes and shapes are possible. With respect to creating a magnetic field of desired uniformity and strength, slug 5214 can be moved towards magnet 5205, and slug 5222 can be moved towards magnet 5216, thereby adjusting the reluctance obstruction path. In some configurations, thumb screws 5211 can be used to adjust the positions of slugs 5214/5222. The selection of the number and type of thumb screws 5211, or automatic magnet positioning adjuster (not shown), can be based at least in part on the strength of magnets 5205/5216. In some configurations, to enable the movement of slugs 5214/5222 during adjustment, slugs 5214/5222 can be surrounded by non-stick material, such as, for example, but not limited to, a material coated with a TEFLON® finish. Any number of slugs and magnets can be used, as long as a uniform magnetic field of the desired strength is created. In some configurations, slugs 5214/5222 can be held in place by fasteners such as, for example, but not limited to, c-clips. At least one effluent tube (not shown) can be securely positioned within specimen mounts 5203/5209. Any form of stabilization for the effluent tube can be used. In some configurations, multiple of bioreactors 5111 (FIG. 5) can produce separate streams of effluent and can require multiple effluent tubes (not shown). Specimen mounts 5203/5209 can accommodate multiple effluent tubes (not shown) and can accommodate the geometry of magnetic field path 5301 (FIG. 7). Spreaders 5201/5215 can enable uniformity in the magnetic field across the sample, and the amount of the adjustment can depend on the geometry of spreaders 5201/5215. Spreaders 5201/5215 can include a single unit, or can include multiple units, possibly operably coupled. In some configurations, the shape of spreaders 5201/5215 can accommodate the geometry of specimen mounts 5203/5209. In some configurations, system 5101A can include parts that can, collectively, weigh approximately ten pounds, and can be manufactured economically, for example, for under 500 USD. A magnetic field path can be formed by frame elements 5223/5224/ 5202/5212/5213 (FIG. 6D). The shape and thickness of frame elements 5223/5224/5202/5212/5213 (FIG. 6D), and their relationship to one another, can vary depending on the desired shape and size of the frame. In some configurations, elements 5223/5224/5212/5213 (FIG. 6D) can overlap elements 5202 (FIG. 6D) at both ends.

Referring now to FIG. 7, energy from uniform magnetic field 5301 can be applied to an effluent, and a transmitting coil can pulse non-ionizing waves across the effluent. The pulsed non-ionizing waves can excite the nuclear spin energy transition of the effluent. The gradient of uniform magnetic field 5301 can be uniform within the measured bandwidth, and can localize the resulting signal in space. Uniform magnetic field 5301 can surround the effluent that can circulate through bioreactor 5111 (FIG. 5) and the effluent tube (not shown). Bioreactor 5111 (FIG. 5) can surround growing tissue, for example. RF transmitter 5121 (FIG. 5) can supply RF signal 121 (FIG. 5) to a transmitter coil (not shown). The choice of the frequency of RF signal 121 (FIG. 5) can be based upon the atomic structure of the sample and uniform magnetic field 5301. Uniform magnetic field 5301 orients the atoms in the sample, and pulsing RF signal 121 (FIG. 5) across the sample makes the atoms resonate at a characteristic frequency that depends on the magnetic field strength. When RF signal 121 (FIG. 5) ceases pulsing, receiver 5123 can detect echo signal 124 (FIG. 5) from the sample.

Figure 8:
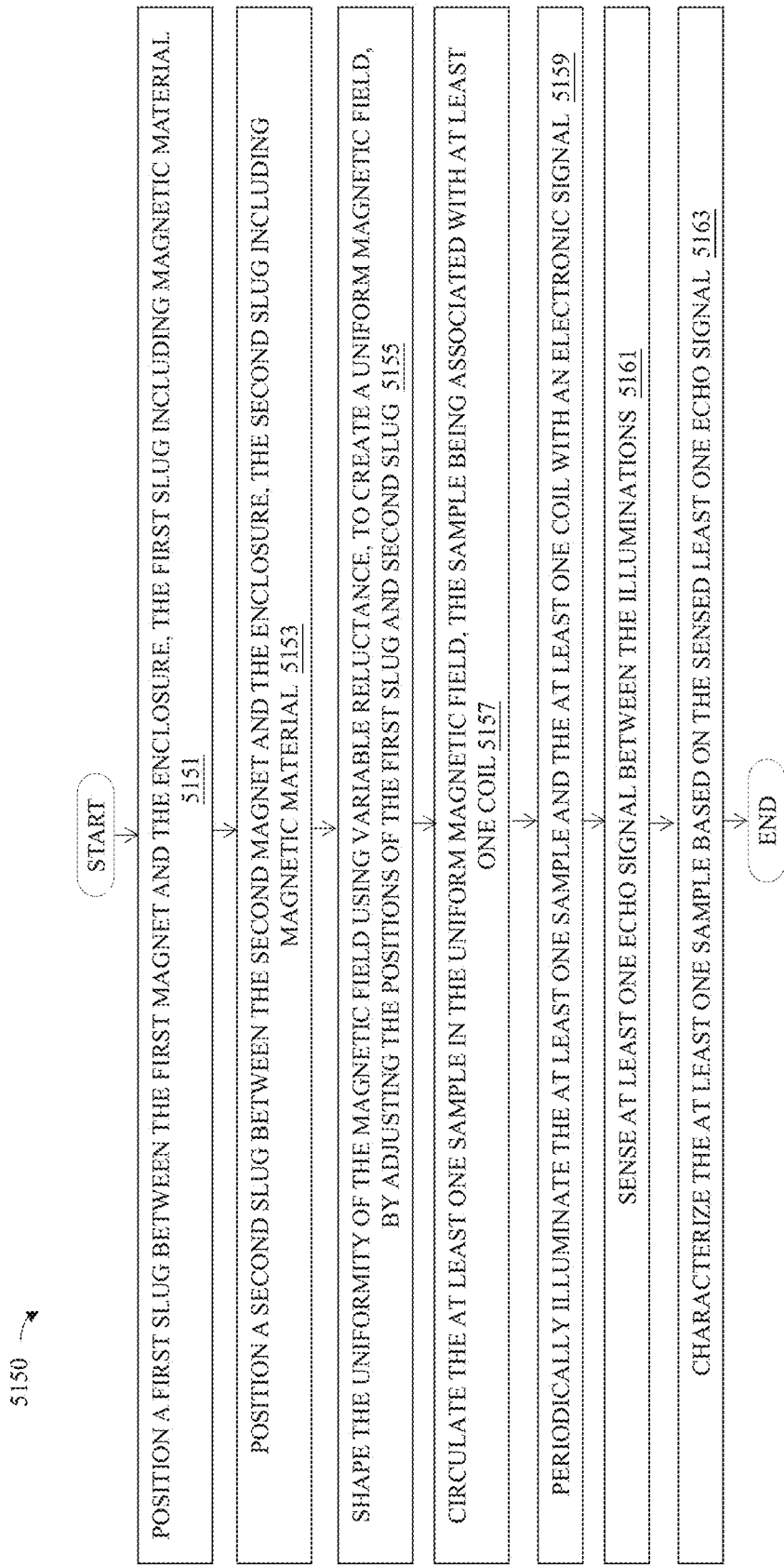
FIG. 8 is a flowchart of the method for characterizing effluent of the present teachings.

Referring now to FIG. 8, method 5150 for characterizing at least one sample from at least one bioreactor using a magnetic resonance apparatus, the magnetic resonance apparatus having a first magnet and a second magnet, the first magnet and the second magnet positioned a pre-selected distance from one another to set up a magnetic field, the first magnet and the second magnet positioned within an enclosure forming a path for the magnetic field, the method can include, but is not limited to including, positioning 5151 a first slug between the first magnet and the enclosure. The first slug can include magnetic material. Method 5150 can include positioning 5153 a second slug between the second magnet and the enclosure. The second slug can include magnetic material. Method 5150 can include shaping 5155 the uniformity of the magnetic field using variable reluctance, to create a uniform magnetic field, by adjusting the positions of the first slug and second slug. Method 5150 can include circulating 5157 the at least one sample in the uniform magnetic field. The sample can be associated with at least one coil. Method 5150 can include periodically illuminating 5159 the at least one sample and the at least one coil with an electronic signal, sensing 5161 at least one echo signal between the illuminations, and characterizing 5163 the at least one sample based on the sensed least one echo signal.

Configurations of the present teachings are directed to computer systems for accomplishing the methods discussed in the description herein, and to computer readable media containing programs for accomplishing these methods. The raw data and results can be stored for future retrieval and processing, printed, displayed, transferred to another computer, and/or transferred elsewhere. Communications links can be wired or wireless, for example, using cellular communication systems, military communications systems, and satellite communications systems. Parts of system 100 (FIG. 1), system 100A (FIG. 1A), system 100B (FIG. 1B), and system 5100 (FIG. 5), for example, can execute on a computer having a variable number of CPUs. Other alternative computer platforms can be used.

The present configuration is also directed to hardware, firmware, and software for accomplishing the methods discussed herein, and computer readable media storing software for accomplishing these methods. The various modules described herein can be accomplished by the same CPU, or can be accomplished on a different computer. In compliance with the statute, the present configuration has been described in language more or less specific as to structural and methodical features. It is to be understood, however, that the present configuration is not limited to the specific features shown and described, since the means herein disclosed comprise preferred forms of putting the present configuration into effect.

Methods 150 (FIG. 4) and 5150 (FIG. 8), can be, in whole or in part, implemented electronically. Signals representing actions taken by elements of system 100 (FIG. 1), system 100A (FIG. 1A), system 100B (FIG. 1B), and system 5100 (FIG. 5), for example, and other disclosed configurations can travel over at least one live communications network. Control and data information can be electronically executed and stored on at least one computer-readable medium. The systems can be implemented to execute on at least one computer node in at least one live communications network. Common forms of at least one computer-readable medium can include, for example, but not be limited to, a floppy disk, a flexible disk, a hard disk, magnetic tape, or any other magnetic medium, a compact disk read only memory or any other optical medium, punched cards, paper tape, or any other physical medium with patterns of holes, a random access memory, a programmable read only memory, and erasable programmable read only memory (EPROM), a Flash EPROM, or any other memory chip or cartridge, or any other medium from which a computer can read. Further, the at least one computer readable medium can contain graphs in any form, subject to appropriate licenses where necessary, including, but not limited to, Graphic Interchange Format (GIF), Joint Photographic Experts Group (JPEG), Portable Network Graphics (PNG), Scalable Vector Graphics (SVG), and Tagged Image File Format (TIFF).

While the present teachings have been described above in terms of specific configurations, it is to be understood that they are not limited to these disclosed configurations. Many modifications and other configurations will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. A system for characterizing at least one sample comprising:
   a plurality of bioreactors producing the at least one sample;
   a plurality of coils receiving and processing information from the plurality of bioreactors simultaneously;
   a plurality of magnetic resonance devices including:
      an enclosure forming a path for a magnetic field, the enclosure including a plurality of cavities accommodating a first magnet, a second magnet, a first positioning means, a second positioning means, a first slug, and a second slug, the first magnet and the second magnet positioned a pre-selected distance from one another within two of the cavities, the first slug positioned between the first magnet and the enclosure, the first slug including magnetic material, the second slug positioned between the second magnet and the enclosure, the second slug including magnetic material; and
      a controller controlling the first positioning means and the second positioning means to position the first slug and the second slug to shape the uniformity of the magnetic field using variable reluctance to create a uniform magnetic field, the controller configured to enable circulation of the at least one sample in the magnetic field, the at least one sample being associated with at least one of the plurality of coils, the controller configured to periodically illuminate the at least one sample and the at least one of the plurality of coils with at least one signal, the controller configured to receive at least one echo signal between the illuminations, the controller characterizing the at least one sample based on the received at least one echo signal; and
   at least one switch operably coupling the plurality of bioreactors with the plurality of magnetic resonance devices, at least one control/data signal originating in a first of the plurality of magnetic resonance devices being routed through the at least one switch to a second of the plurality of magnetic resonance devices.

2. The system as in claim 1 further comprising:
a sample tube encircled by the at least one coil, the sample tube resting between the first magnet and the second magnet, the sample tube providing a channel for the at least one sample.

3. The system as in claim 1 further comprising:
a resonator shaping the at least one echo signal.

4. The system as in claim 1 wherein each of the at least one switch comprises:
a plurality of poles, each of the plurality of poles configured to control each pair of the plurality of bioreactors and the plurality of magnetic resonance devices separately.

5. The system as in claim 1 wherein the plurality of coils comprises:
a matrix.

6. The system as in claim 1 wherein the first magnet comprises:
a rotatable magnet.

7. The system as in claim 6 further comprising:
at least one container including the at least one sample, the at least one container positioned in proximity to the rotatable magnet.

8. The system as in claim 6 further comprising:
an adjustment means rotating the rotatable magnet to adjust the strength of the magnetic field.

9. The system as in claim 1 further comprising:
a transmitter periodically transmitting the at least one signal across the at least one sample, the at least one signal energizing the at least one sample, the controller controlling the transmitter.

10. The apparatus as in claim 9 further comprising:
a resonator shaping the transmitted at least one signal.

11. The system as in claim 9 further comprising:
a temperature sensor providing temperature data to the controller, the controller commanding the transmitter to adjust, based on the temperature data, a center frequency of the at least one signal to accommodate magnetic drift.

12. The system as in claim 1 wherein the at least one signal comprises:
a non-ionizing signal.

13. The system as in claim 1 further comprising:
a receiver receiving the at least one echo signal, the controller controlling the receiver.

14. The apparatus as in claim 13 further comprising:
a resonator shaping the received at least one echo signal.

15. The system as in claim 1 further comprising:
a spreader operably positioned between the first magnet and the second magnet, the spreader configured to enable uniformity of the magnetic field.

16. The system as in claim 15 wherein the first magnet comprises a diametric magnetization vector, the diametric magnetization vector being substantially perpendicular to the spreader.

17. The system as in claim 1 further comprising:
a positioner adjusting the strength of the magnetic field based on a position of the second magnet.

18. The system as in claim 17 wherein the positioner responds to the commands from the controller.

19. The system as in claim 1 further comprising an electronic signal generator, the generator supplying the at least one signal, the generator responding to the commands from the controller.

* * * * *